(12) United States Patent
Garcia et al.

(10) Patent No.: US 9,689,856 B2
(45) Date of Patent: Jun. 27, 2017

(54) NON-DESTRUCTIVE METHODS FOR NOBLE METAL LOADING ANALYSIS ON MATERIAL SURFACES

(71) Applicant: Electric Power Research Institute, Palo Alto, CA (US)

(72) Inventors: Susan Elaine Garcia, Paso Robles, CA (US); Thomas Pompilio Diaz, San Martin, CA (US); Samson Hettiarachchi, Menlo Park, CA (US); Rajeshwar Singh Pathania, Sunnyvale, CA (US)

(73) Assignee: ELECTRIC POWER RESEARCH INSTITUTE, Palo Alto, CA (US)

( * ) Notice: Subject to any disclaimer, the term of this patent is extended or adjusted under 35 U.S.C. 154(b) by 0 days.

(21) Appl. No.: 15/094,892

(22) Filed: Apr. 8, 2016

(65) Prior Publication Data
US 2016/0299115 A1    Oct. 13, 2016

Related U.S. Application Data

(60) Provisional application No. 62/146,139, filed on Apr. 10, 2015.

(51) Int. Cl.
*G01N 33/20* (2006.01)
*G21C 17/01* (2006.01)
*G21C 17/017* (2006.01)

(52) U.S. Cl.
CPC ............. *G01N 33/20* (2013.01); *G21C 17/01* (2013.01); *G21C 17/017* (2013.01); *Y10T 436/206664* (2015.01)

(58) Field of Classification Search
CPC .......... G01N 33/20; Y10T 436/206664; Y10T 436/2575; G21C 17/00; G21C 17/01; G21C 17/017
(Continued)

(56) References Cited

U.S. PATENT DOCUMENTS 2,721,788 A    8/1950    Schad
3,347,630 A    10/1967    Baumgartner et al.
(Continued)

OTHER PUBLICATIONS

Hettiarachchi et al., Corrosion/95 Paper/#95410, NACE International, Orlando, Florida, Mar. 1995; "A Novel Approach for Nobel Metal Deposition on Surfaces for IGSCC Mitigation of Boiling Water Reactor Internals," 9 pages.
(Continued)

*Primary Examiner* — Maureen Wallenhorst
(74) *Attorney, Agent, or Firm* — Dergosits & Noah LLP

(57) ABSTRACT

Compositions and methods are provided for assessing the presence or absence, and optionally quantitating, the surface loading of a noble metal such as platinum on the surface of a substrate. The invention utilizes the decomposition rate of hydrogen peroxide ($H_2O_2$) or other redox active molecule following exposure to the substrate surface to effectively establish a qualitative or quantitative correlation between the redox agent survival fraction and the presence or absence of noble metal (e.g., platinum), and further, for the quantitation of noble metal loading on the substrate surface. The invention finds applicability in assessing the surface loading of noble metals on the internal surfaces of boiling water nuclear reactor plants (BWR) that have undergone prior noble metal application.

18 Claims, 14 Drawing Sheets

(58) Field of Classification Search
USPC ............... 436/73, 80, 81, 84, 135, 180, 904; 422/53, 501; 376/245, 249
See application file for complete search history.

(56) References Cited

U.S. PATENT DOCUMENTS

| | | | | |
|---|---|---|---|---|
| 5,287,392 | A | * | 2/1994 | Cowan, II ................ B01J 35/04 376/301 |
| 5,581,588 | A | * | 12/1996 | Andresen ................ C23F 11/00 106/1.15 |
| 5,625,656 | A | * | 4/1997 | Hettiarachchi ........ B01J 37/031 376/245 |
| 5,711,146 | A | | 1/1998 | Armstrong et al. |
| 5,818,893 | A | * | 10/1998 | Hettiarachchi ........ B01J 37/031 376/305 |
| 6,440,297 | B1 | * | 8/2002 | Kim ..................... G01N 27/423 204/400 |
| 2002/0080906 | A1 | * | 6/2002 | Andresen ................ C23F 11/18 376/306 |

OTHER PUBLICATIONS

Hettiarachchi et al., 8th Int. Conference on Env. Degradation of Materials in Nuclear Power Systems-Water Reactors, Aug. 10-14, Amelia Island, Florida, 1997; "Corrosion and Redox Potential Measurements in German Pressurized and Boiling Water Reactors," 9 pages.

Hettiarachchi, 10th Int. Conference on Env. Degradation of Materials in Nuclear Power Systems-Water Reactors, Aug. 5-9, Lake Tahoe, Nevada, 2001; "Noble Metal Chemical Addition From Concept to Operating Commercial Power Plant Application," 19 pages.

Hettiarachchi and Diaz, International Water Chemistry Conference, Seoul, Korea, Oct. 2006; "The On-Line NobleChem(TM) Application Experience in an Operation BWR," 7 pages.

Hettiarachchi and Diaz, International Water Chemistry Conference, Jeju Island, Korea, Oct. 2006; "The On-Line NobleChem(TM) Application Experience in an Operation BWR," 7 pages.

Hettiarachchi and Diaz, 15th International Conference on Nuclear Engineering (ICONE-15), Apr. 22-26, Nagoya, Japan, 2007; "Noble Metal Injection During Power Operation for BWR Crack Mitigation and Dose Rate Reduction," 9 pages.

Hettiarachchi et al., 13th International Conference on Environmental Degradation of Materials in Nuclear Power Systems, Whistler, Canada, Aug. 19-23, 2007; "NobleChem(TM) Application During Power Operation for Crack Mitigation and Dose Rate Reduction of BWRs," 10 pages.

Hettiarachchi et al., 14th International Conference on Environmental Degradation of Materials in Nuclear Power Systems, Virginia Beach, Virginia, Aug. 2009; "Electrochemical Corrosion Potential (ECP) Reduction and Crack Mitigation Experiences With NobleChem(TM) and On-Line NobleChem(TM)," 20 pages.

Lin and Smith, "Decomposition of hydrogen peroxide at elevated temperatures," Electric Power Research Institute, EPRI ID NP-6733 (Mar. 1990); 144 pages.

Hettiarachchi et al., "The Concept of Noble Metal Chemical Addition Technology for IGSCC Mitigation of Nuclear Materials," 7th Int. Symposium on Env. Degradation of Materials in Nuclear Power Systems-Water Reactors, Breckenridge, Colorado (Aug. 7-10, 1995).

Lu and Zangari, "Electrodeposition of Platinum Nanoparticles on Highly Oriented PyroliticGraphite Part II: Morphological Characterization by Atomic Force Microscopy," Electrochimica Acta, 51:2531-2538 (2006).

MacInnes, "The mechanism of the catalysis of hydrogen peroxide by colloidal Pt," J. of American Chemical Society, 36(5):878-881 (1914).

Rooth et al., "Hydrogen Peroxide in BWRs: an experimental determination of the actual level," Water Chemistry of Nuclear Reactor Systems 5, vol. 2, British Nuclear Energy Society, London, UK (Oct. 23-27, 1989).

Electric Power Research Institute, "BWRVIP-43: In-Plant Demonstration of Noble Metal Chemical Addition at Duane Arnold Energy Center," Product ID TR-108702, published 1997; abstract only on 3 pages.

Electric Power Research Institute, "BWRVIP-62 Revision 1: BWR Vessel and Internals Project, Technical Basis for Inspection Relief for BWR Internal Components with Hydrogen Injection," Product ID: 1022844 (2011); abstract only on 3 pages.

Electric Power Research Institute, "BWRVIP-62-A: BWR Vessel and Internals Project, Technical Basis for Inspection Relief for BWR Internal Components with Hydrogen Injection," Product ID: 1021006 (2010); abstract only on 3 pages.

Electric Power Research Institute, "BWRVIP-238: BWR Vessel and Internals Project, On-Line NobleChem™ Electrochemical Corrosion Potential and Pt Loading Data Correlation for Plants," Product ID 1020875 (2010); abstract only on 3 pages.

* cited by examiner

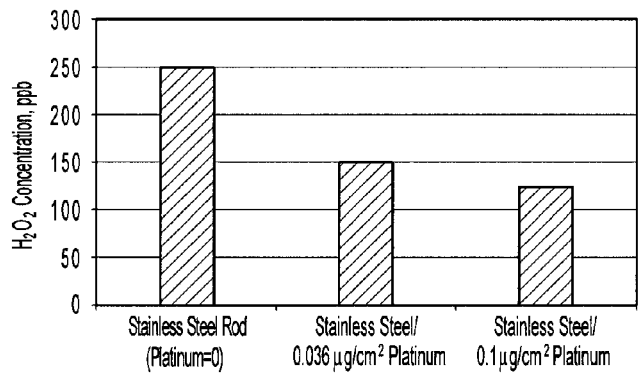

FIG. 12

| Type 304 Stainless Stee Heat # E110333 | | | | | | | | | | | | | | |
|---|---|---|---|---|---|---|---|---|---|---|---|---|---|---|
| C | Mn | Si | P | S | Cr | Ni | Mo | Cu | Cb/Ta | Ti | Co | Al | Sn | V | N |
| 0.23 | 1.82 | 0.227 | 0.033 | 0.028 | 18.13 | 8.08 | 0.33 | 0.383 | 0.006 | 0.02 | 0.141 | 0.002 | 0.013 | 0.06 | 0.076 |
| YS KSI | TS KSI | Elong % | %RA % | Hardness HB | Grain Size # | | | | | | | | | | |
| 71.5 | 97 | 50 | 75 | 197 | 5 | | | | | | | | | | |

FIG. 13

| Test # | Injectant % $CH_3OH$ | Injectant Flow (ccpm) | Loop Flow (ccpm) | Total Flow (ccpm) | Injection Time (minutes) | Temperature (°C) | Pressure (psi (Mpa)) | Test Specimen Type |
|---|---|---|---|---|---|---|---|---|
| $CH_3OH$ #1 | 20 | 5 | 45 | 50 | 10 | 250 | 600 (4.16) | Platinum foil Flag |
| $CH_3OH$ #2 | 80 | 5 | 45 | 50 | 10 | 250 | 600 (4.16) | Platinum foil Flag |

FIG. 14

| Test # | Injectant HCHO (ppm) | Injectant $H_2O_2$ (ppm) | Injectant Flow (ccpm) | Loop Flow (ccpm) | Total Flow (ccpm) | Injection Time (minutes) | Test Temperature (°C) | Test Pressure (psi (Mpa)) | Test Pspecimen Type |
|---|---|---|---|---|---|---|---|---|---|
| HCHO #1 | 2500 | 0 | 5 | 45 | 50 | 10 | 250 | 600 (4.16) | Platinum foil Flag |
| HCHO #2 | 3846 | 1.08 | 5 | 45 | 50 | 10 | 250 | 600 (4.16) | Platinum foil Flag |

FIG. 15

| Test # | Injectant HCHO (ppm) | Injectant $H_2O_2$ (ppm) | Injectant Flow (ccpm) | Loop Flow (ccpm) | Total Flow (ccpm) | Injection Time (minutes) | Test Temperature (°C) | Test Pressure (psi (Mpa)) | Test Pspecimen Type |
|---|---|---|---|---|---|---|---|---|---|
| HCHO #3 | 11538 | 1.08 | 5 | 45 | 50 | 10 | 250 | 600 (4.16) | Platinum foil Flag |
| HCHO #3 LF | 11538 | 1.08 | 1 | 9 | 10 | 10 | 250 | 600 (4.16) | Platinum foil Flag |
| HCHO #4 | 11538 | 1.08 | 5 | 45 | 50 | 10 | 250 | 600 (4.16) | Stainless Steel Rod |
| HCHO #4 LF | 11538 | 1.08 | 1 | 9 | 10 | 10 | 250 | 600 (4.16) | Stainless Steel Rod |
| HCHO #5 | 11538 | 1.08 | 5 | 45 | 50 | 10 | 250 | 600 (4.16) | Abraded Stainless Stee + Platinum |
| HCHO #5 LF | 11538 | 1.08 | 1 | 9 | 10 | 10 | 250 | 600 (4.16) | Abraded Stainless Stee + Platinum |

FIG. 16

Test Conditions for 3.5 ppm $H_2O_2$ Injection 5 ccpm at two High Temperatures

| Test Specimen Type | Test Temperature (°C) | Test Pressure (psi (Mpa)) | Injectant Flow (ccpm) | Loop Flow (ccpm) | Injectant Concentration (ppm) |
|---|---|---|---|---|---|
| stainless steel rod | 125 | 600 (4.16) | 5 | 0 | 3.720 |
| stainless steel rod | 150 | 600 (4.16) | 5 | 0 | 3.720 |
| abraded stainless steel with 0.1 μg/cm² platinum | 125 | 600 (4.16) | 5 | 0 | 3.230 |
| abraded stainless steel with 0.1 μg/cm² platinum | 150 | 600 (4.16) | 5 | 0 | 3.230 |
| platinum foil flag | 125 | 600 (4.16) | 5 | 0 | 3.230 |
| platinum foil flag | 150 | 600 (4.16) | 5 | 0 | 3.230 |

FIG. 17

Results of Hydrogen Peroxide Injection at 125°C and 150°C

| Test Specimen | Test Temp (°C) | Injectant (ppm) | Sample $H_2O_2$ (ppm) | Survival Fraction |
|---|---|---|---|---|
| stainless steel rod | 125 | 3.720 | 3.500 | 0.941 |
| stainless steel rod | 150 | 3.720 | 1.580 | 0.425 |
| abraded stainless steel with 0.1 μg/cm² platinum | 125 | 3.230 | 1.410 | 0.435 |
| abraded stainless steel with 0.1 μg/cm² platinum | 150 | 3.230 | 1.220 | 0.379 |
| platinum foil | 125 | 3.230 | 1.000 | 0.310 |
| platinum foil | 150 | 3.230 | 0.800 | 0.248 |

FIG. 18

- Hydrogen peroxide reduction or oxidation

Expected reaction : $H_2O_2 + 2H^+ + 2e \rightarrow 2 H_2O$ $H_2O_2 \rightarrow O_2 + 2H^+ + 2e$ Expect redox response depending on Platinum loading

- Methanol Oxidation

Expected reaction : $CH_3OH + O_2 \rightarrow HCOOH + H_2O$

- Ethanol Oxidation

Expected reaction : $C_2H_5OH + O_2 \rightarrow CH_3COOH + H_2O$

- HCHO Oxidation

Expected reaction : $HCHO + \frac{1}{2} O_2 \rightarrow HCOOH$

FIG. 19

NON-DESTRUCTIVE METHODS FOR NOBLE METAL LOADING ANALYSIS ON MATERIAL SURFACES

CROSS-REFERENCE TO RELATED APPLICATIONS

This application claims priority to and benefit of U.S. Provisional Application Ser. No. 62/146,139, filed on Apr. 10, 2015, which is herein incorporated by reference in its entirety.

FIELD OF THE INVENTION

The invention relates generally to improved methods for assessing and quantitating the loading of noble metals such as platinum on the internal surfaces of boiling water nuclear reactor plants (BWR) that have undergone noble metal chemical application (NMCA) or on-line noble metal chemical application (OLNC).

BACKGROUND OF THE INVENTION

The boiling water reactor (BWR) is a light water nuclear reactor used for the generation of electrical power. The BWR uses demineralized water as a coolant and neutron moderator. In a BWR, heat is produced by nuclear fission in the reactor core. The heat causes the cooling water to boil, producing steam, which is directly used to drive a steam turbine. The steam is then cooled in a condenser and converted back to liquid water. This water is then returned to the reactor core, completing the loop.

BWR internal surfaces are most commonly formed from one of the three major structural materials used in the nuclear industry. These are stainless steel (typically type 304), INCONEL® nickel-chromium-iron alloy 600 and INCONEL® alloy 182. These internal surfaces are subjected to significant tensile stresses during operation, including elevated temperatures and/or elevated pressures, and are prone to stress corrosion cracking (SCC).

The presence of noble metals deposited onto reactor internal surfaces can reduce the internal surface susceptibility to stress corrosion cracking. A simple method of applying a noble metal such as platinum (Pt) to reactor internals involves adding a solution of a noble metal compound into reactor water to cause deposition of noble metal onto contacted surfaces. This noble metal chemical addition (NMCA) technology is now widely used in BWR utilities. The NMCA treatment of surfaces has drastically lowered the hydrogen demand necessary for intergranular stress corrosion cracking (IGSCC) protection of the materials forming the internal surfaces of the reactor. A variation of this methodology for applying a noble metal on all reactor surfaces employs the reactor coolant water as the medium of transport for depositing the noble metal, a process called on-line NMCA or OLNC. The noble metal surface doping results in reactor surfaces that exhibit noble-metal-like behavior that are more resistant to reactor conditions and show reduced levels of stress corrosion cracking. These noble metal applications can be applied to most of the structural materials used in nuclear power generation.

A majority of the BWRs in the United States, and a smaller number abroad, employ NMCA in combination with low hydrogen water chemistry (HWC) that improves the effectiveness of recombination of $H_2$ and oxidants to achieve low electrochemical corrosion potentials (ECP) (Hettiarachchi et al., CORROSION/95 Paper#95410, NACE International, Orlando, Fla., March 1995.). Typical NMCA applications (injection of noble metals into the reactor water) are performed just prior to an outage at a temperature of 240 to 290° F. (116 to 148° C.) (Hettiarachchi et al., 7th Int. Conference on Env. Degradation of Materials in Nuclear Power Systems-Water Reactors, August 7-10, Breckenridge, Colo., 1995; Hettiarachchi et al., 8th Int. Conference on Env. Degradation of Materials in Nuclear Power Systems-Water Reactors, August 10-14, Amelia Island, Fla., 1997; In-Plant Demonstration of NMCA at Duane Arnold Energy Center, BWRVIP-43, EPRI-TR108702, September, 1997; Hettiarachchi, 10th Int. Conference on Env. Degradation of Materials in Nuclear Power Systems-Water Reactors, August 5-9, Lake Tahoe, Nev., 2001). All added chemical species are cleaned-up during application and during the outage, before the plant resumes its start-up operation.

NMCA has been further developed so that noble metals at very low concentrations (parts per trillion; ppt) can be injected into the coolant while the plant is operating at full power. This process of on-line NMCA (OLNC) has been applied at a reactor water temperature of 530 to 540° F. (277 to 282° C.) (Hettiarachchi and Diaz, International Water Chemistry Conference, Seoul, Korea, October, 2006; Hettiarachchi and Diaz, 15th International Conference on Nuclear Engineering (ICONE-15), April 22-26, Nagoya, Japan, 2007; Hettiarachchi et al., 13th International Conference on Environmental Degradation of Materials in Nuclear Power Systems, Whistler, Canada, Aug. 19-23, 2007; Hettiarachchi et al., 14th International Conference on Environmental Degradation of Materials in Nuclear Power Systems, Virginia Beach, Va., August, 2009). In addition, OLNC is expected to deposit noble metal inside cracks more efficiently because of their more open nature during plant operation and the higher coolant flow rates. The advantage of NMCA or OLNC is that they require very little hydrogen addition into the feedwater (0.15 to 0.35 parts per million; ppm) to achieve low electrochemical corrosion potentials (ECPs), thus minimizing operating dose rate concerns. OLNC uses the electrocatalytic effect of platinum to efficiently recombine $O_2$ and $H_2O_2$ with $H_2$ on the metal surface at low feedwater hydrogen concentrations.

OLNC uses just one noble metal chemical ($Na_2Pt(OH)_6$), and the first OLNC plant demonstration was successfully completed in 2005 while the reactor was in power operation (Hettiarachchi and Diaz, International Water Chemistry Conference, Jeju Island, Korea, October, 2006). When injected into BWR environments, the noble metal particles deposit on oxidized stainless steel surfaces and lower the corrosion potential in the presence of low hydrogen, which decreases the propensity for IGSCC.

A unique feature of OLNC is the achievement of low ECP within 8 to 24 hours of the addition of parts per trillion levels of platinum into the feedwater of operating BWRs (Hettiarachchi et al., 13th International Conference on Environmental Degradation of Materials in Nuclear Power Systems, Whistler, Canada, Aug. 19-23, 2007). This response has been observed at many OLNC BWRs in both internal (reactor recirculation system or RRS) and external ECP measurement locations (material monitoring system or MMS) (Hettiarachchi et al., 14th International Conference on Environmental Degradation of Materials in Nuclear Power Systems, Virginia Beach, Va., August, 2009).

The fact that ECP reaches low values within a short time during the OLNC application indicates that the amount of platinum loading required to generate catalytic activity on stainless steel surfaces is quite small. In fact, the amount of platinum loading after a 10 day OLNC application has also been quite low (0.01 µg/cm$^2$) in many instances posing a challenge to measuring the low platinum loadings. The actual amount of platinum loading required to achieve low ECPs in the presence of low hydrogen can in fact be a factor of ten lower (0.001 µg/cm$^2$), based on an analysis performed to determine the correlation between the surface ECP and platinum loading (Hettiarachchi and Wehlage, BWRVIP-238, EPRI Report 1020875, January, 2010). Measuring this amount of platinum on an MMS surface by the aqua regia digestion and analysis is beyond the capability of an ICPMS by the current approach, unless the solution is concentrated by evaporation to elevate the platinum concentration in solution to measurable levels. However, ECP is able to detect the catalytic activity even at these low loading levels. Unfortunately, it is observed that ECP is not sensitive enough to detect the difference between a platinum loading of 0.001 and 0.005 µg/cm$^2$.

FIG. 5 shows a possible explanation for why the actual platinum loading required for electrochemical corrosion potential (ECP) reduction (0.001 µg/cm$^2$) might be much lower than the amount of platinum loading that is measured by stripping of the oxide, digestion and analysis by inductively coupled plasma mass spectrometry (0.01 to 0.05 µg/cm$^2$). In FIG. 5, the oxidized surface 540 of a stainless steel substrate 505, as might be used in a material monitoring system, is depicted. The oxidized stainless steel surface 540 is associated with catalytically reactive platinum 500 in the catalytically accessible surface layer 530, as well as less-reactive platinum 502 contained in the catalytically inaccessible inner layer 520 not directly exposed to the reaction solution.

The less-reactive platinum 502 in the catalytically inaccessible inner layer 520 is underneath larger crud/oxide particles 510. The low ECP response is a surface property that is controlled by the catalytically active outer surface layer 530 containing catalytically accessible platinum 500, while the total platinum loading (as measured by oxide stripping, digestion and inductively coupled plasma mass spectrometry) analyzes the platinum contained in both the catalytically accessible surface layer 530 as well as platinum in the catalytically inaccessible inner layer 520 in the bulk of the crud/oxide 510 found in the catalytically inaccessible inner layer 520. Catalytically inactive (or less reactive) platinum 502 in the inner platinum layer 520 contributes little, if any, to the observed ECP response.

Thus, the parameter that reduces electrochemical corrosion potential following NMCA or OLNC is most likely the surface catalysis and deposition of platinum that occurs in the outer layer 530, not the platinum loading in the crud/oxide 510 found in the inner layer 520. It is possible that there might be instances when the measured platinum loading shows significant values, but the actual ECP response might be sluggish if most of the platinum resides in the oxide layer underneath the surface layer 530. Therefore, relying on the total platinum loading (as measured by inductively coupled plasma mass spectrometry, or ICPMS) could lead to potential errors, while a surface catalytic measurement would unequivocally correlate more closely to the low ECPs. Hettiarachchi and Wehlage, BWRVIP-238, EPRI Report 1020875, January, 2010.

EPRI documents BWRVIP-62 and BWRVIP-62A require that utilities that have performed noble metal chemical application (NMCA) or on-line noble metal chemical applications (OLNC) to prove that sufficient loading of the noble metal exist on plant internal surfaces. These BWRs face the challenging issue of determining the amount of noble metal on reactor internal surfaces for the purpose of obtaining inspection relief.

The current traditional approach to determine noble metal deposition involves allowing reactor water to flow through a materials monitoring system (MMS) that consists of a series of 0.5 to 0.75 inch internal diameter (ID) oxidized stainless steel tubing fitted together with SWAGELOK® fittings, during NMCA or OLNC applications. During or at the end of the application, MMS tubing sections are removed, cut in to three sections, and the internal diameter oxide containing the noble metal is stripped by dissolving with hot aqua regia digestion near boiling temperature to release the metal, resulting in a solution that is analyzed for the noble metal content using an inductively coupled plasma mass spectrometer (ICPMS). The noble metal concentration in the solution is then converted to a mass loading value (µg/cm$^2$) by taking into account the surface area of the stripped section.

This traditional approach is labor and time intensive, and is plagued with drawbacks. First, the traditional methods are destructive, resulting in the removal of the oxide from the surfaces, for example, from a stainless steel surface. Second, the method requires digestion of the oxide in aqua regia, near boiling temperature, to dissolve the noble metal, such as platinum. Aqua regia, or nitro-hydrochloric acid, is a highly corrosive mixture of acids that is prone to mishandling. Third, the traditional assay method requires the use of ICPMS for the noble metal (e.g., platinum) analysis. ICPMS is an expensive instrumentation that is typically not available in BWR utilities. In addition to the expense, the use of ICPMS is problematic because the platinum loading results obtained have (e.g., 0.01 µg/cm$^2$) approach the lower detection limits of the ICPMS instrumentation, thereby creating potential uncertainty in the loading values. This approach often requires the BWR utility to remove an MMS section periodically and ship to a vendor for processing and analysis, resulting in significant delays in obtaining the loading data.

What is needed in the art are rapid, reliable, non-destructive methods for assessing and quantitating the loading of noble metals such as platinum on plant internal surfaces that have performed NMCA/OLNC applications. Ideally, these methods can be conducted at the plant site. This will greatly facilitate the process for obtaining inspection relief, and would be of great value to the BWR utilities.

The present invention, in its many embodiments, provides solutions to these problems, have a number of advantages over the state of the art and provide many benefits previously unrealized in other types of methods. In addition, still further benefits flow from the invention described herein, as will be apparent upon reading the present disclosure.

Aspects of the general state of the art can be found in various sources, for example, Lin and Smith, "Decomposition of hydrogen peroxide at elevated temperatures", EPRI Project NP-6733 (March 1990); Macinnes, "The mechanism of the catalysis of hydrogen peroxide by colloidal Pt," J. of American Chemical Society, 36(5):878-881 (1914); Rooth and Ullberg, "Hydrogen Peroxide in BWRs", Water Chemistry of Nuclear Reactor Systems 5, Vol. 2, British Nuclear Energy Society, London, UK (Oct. 23-27, 1989); U.S. Pat. No. 2,721,788, to Chad, entitled "A reaction for hydrogen peroxide decomposition"; U.S. Pat. No. 3,347,630, to Baumgart, entitled "Hydrogen peroxide decomposition"; and U.S. Pat. No. 5,711,146, to Armstrong and Toombs, entitled "Hydrogen peroxide decomposition." The present invention provides advantages previously unrealized over the state of the art.

SUMMARY OF THE INVENTION

The present invention provides methods for assessing and quantitating the loading of noble metals such as platinum on substrate surfaces, for example, the internal surfaces of boiling water nuclear reactor plants (BWR) that have undergone prior noble metal chemical application (NMCA) or on-line noble metal chemical application (OLNC). These methods utilize the decomposition of a redox active molecule, for example but not limited to hydrogen peroxide ($H_2O_2$), to effectively establish a correlation between the survival fraction of the redox reagent following exposure to the substrate surface, and the platinum loading on the substrate surface.

Generally, the method involves exposing the surface to be tested, e.g., a stainless steel surface, to a solution of redox reagent such as $H_2O_2$ of known concentration at a selected temperature, allowing $H_2O_2$ decomposition to occur over a period of time and then measuring the remaining $H_2O_2$ content (the survival fraction) in the solution, for example, by using a simple $H_2O_2$ analyzer. The amount of $H_2O_2$ decomposed is a function of the catalytic activity caused by the noble metal, such as platinum, at a given temperature. Since the amount of platinum deposited on the surface is known from the number of coulombs passed from Faraday's law calculations, the decomposed $H_2O_2$ content (the survival fraction) can be correlated to the platinum loading value. Successful proof-of-concept demonstration of the technique is described in the present disclosure. When applied to BWR specimens in the field, the techniques described herein find use when applied either qualitatively or quantitatively.

In some embodiments, the invention provides methods for detecting a noble metal associated with the surface of any substrate of interest, usually where the substrate contains a measurable surface area. The substrate can be any substrate, including rigid substrates and flexible substrates. The inventions are well suited for the analysis of metal substrates, such as stainless steel substrates, where such substrates can be in the form of pipes, tubing, cylindrical chambers, or any kind of enclosed channel. In some aspects, the substrate surface is an oxidized surface.

The substrate analyzed is exposed to a reaction solution comprising at least one redox active molecule that is initially exposed to the substrate at a known concentration. Hydrogen peroxide ($H_2O_2$) finds particular use with the invention. This exposure results in loss of redox active molecule, and measuring a reduction in the concentration of the redox active molecule at the end of the defined reaction period, and under reproducible reaction conditions such as reproducible temperatures (e.g., temperature between about 25° C. and 320° C.) and pressures, indicates the presence of noble metal on the surface of the substrate.

In some embodiments, the invention can be used qualitatively to detect the presence or absence of a noble metal in the substrate surface. In this aspect, the decomposition of any reproducibly detectable and/or significant amount of redox agent following exposure to the substrate surface indicates the presence of noble metal. In contrast, if no decomposition or very low levels of decomposition of the redox agent are observed (e.g., the survival fraction is 100%, nearly 100% or on the order of about 75% to 80%, or values between about 75% to 100%), that is an indication that there is no noble metal, or no detectable levels of noble metal, on the substrate surface. In some embodiments, a decomposition test with a reference sample containing no noble metal is included in the analysis.

In some particularly useful embodiments, the methods of the invention are used quantitatively, where the detection of a particular degree of loss of the redox active molecule in the post-reaction solution correlates with a particular noble metal loading value. In these quantitative methods, a correspondence between loss of the redox active molecule in a post-reaction solution with calibrated noble metal loading values are generally first determined by constructing a standard curve with reference values. The noble metal loading value associated with the surface of the experimental substrate is derived by comparing the experimental loss of redox agent with the table or graph of predetermined noble metal loading values.

The methods of the invention can be adapted for the detection of any noble metal, including ruthenium, rhodium, palladium, silver, osmium, iridium, platinum, gold, mercury, rhenium and copper, although platinum finds particular use with the invention.

In other useful aspects, the invention provides material monitoring system methods for the "in situ" detection of the presence or absence of noble metals associated with the surface of a channel that resides within the reaction chamber, or where that channel is contiguous with the water of the reactor. These methods generally utilize a channel containing a unidirectional liquid flow from the reactor chamber, with an injection port at a first terminus, and a sampling port at a downstream second terminus. A reaction solution comprising at least one redox active molecule at a known concentration is delivered into the liquid flow through the injection port, thereby exposing the surface of the channel to the reaction solution and generating a post-reaction liquid flow. A sample of that flow is extracted through the sampling port. The concentration of the redox active molecule in the extracted sample is determined, and the noble metal associated with the surface of the channel is calculated, either qualitatively or quantitatively. In some aspects, the channel is a substantially cylindrical structure having the same or a similar composition as the walls and/or internal components of the BWR.

In other aspects, the invention provides apparatus and entire monitoring systems, for example, systems for the execution of "in situ" material monitoring of noble metal deposition. These monitoring systems can determine the presence or absence of noble metal such as platinum on a substrate surface, and more advantageously, can quantitate the amount of noble metal present to derive a loading value of the metal. In one example, a system of the invention comprises a channel housing a liquid flow of water from the BWR. This channel contains an injection port operably coupled to the channel, where a redox active reaction solution can be delivered to the liquid flow. There is also a sampling port operably coupled to the channel at a position downstream from the injection port (relative to the direction of liquid flow), where a sample from the liquid flow can be extracted through the sampling port. The sample thus collected can then be analyzed by system instrumentation capable of detecting the redox active molecule.

The system also includes a correlation module capable of correlating the detection of the redox active molecule by the instrumentation with detection and/or quantitation of noble metal deposited onto the surface of the channel. The correlation module can be entirely visual and requires human intervention to correlate the experimental redox molecule quantitation with the noble metal loading value, such as by reading from a standardization curve, or looking up a value from a suitable table or chart. In other aspects, the correlation module is electronic, where the experimental redox molecule quantitation value is delivered to a computer containing algorithm for the execution of instructions for computing the noble metal loading value based on prior-entered standardization data. In some embodiments, the electronic correlation module of the invention can be electronically coupled to the system instrumentation for detecting the redox active molecule, such that the redox molecule quantitation value generated by the instrumentation is delivered automatically by electronic means to a computer containing instructions for the calculation of the noble metal loading value based on prior-entered standardization data, and without human intervention.

BRIEF DESCRIPTION OF THE DRAWINGS

FIG. 9A shows the measured pH over 10 minutes for the platinum flag specimen at a 50 cubic centimeters per minute (ccpm) high flow rate system. FIG. 9B shows the measured pH after 10 minutes for the platinum flag specimen at a 10 ccpm low flow rate system.

FIG. 10A shows the measured pH over 10 minutes of the abraded plus platinum-treated stainless steel specimen at 50 ccpm high flow system. FIG. 10B shows the measured pH over 10 minutes of the abraded plus platinum-treated stainless steel specimen at 10 ccpm low flow system.

FIG. 12 provides a table of results of measurement of catalytic reactivity as measured by final hydrogen peroxide concentration provided as $H_2O_2$ parts per billion (ppb) following a 30 minute catalysis period. The reactions were conducted at 80° C. and compared catalysis results for stainless steel samples with and without platinum, and two different levels of preloaded platinum. Values of 250 ppb indicates no decomposition of the starting $H_2O_2$ concentration.

FIG. 13 provides a description of the chemical and mechanical properties of the Type-304 stainless steel material used in the analysis of hydrogen peroxide catalysis in the presence of platinum that has been deposited on the stainless steel.

FIG. 14 provides testing conditions for methanol ($CH_3OH$) catalysis reactions using platinum foil flag substrate. The read-out was the measured pH of the test section effluent before and after injection of methanol. Test conditions for $CH_3OH$ Tests #1 and #2 were identical, except the injectant methanol concentrations were 20% $CH_3OH$ for test #1 and 80% $CH_3OH$ for test #2.

FIG. 15 provides testing conditions for formaldehyde and $CHOH/H_2O_2$ combination catalysis reactions using platinum foil flag substrate. The read-out was the measured pH of the test section effluent before and after injection of formaldehyde or a $CHOH/H_2O_2$ combination. Test conditions for Tests #1 and #2 were identical, except the test #1 injectant was formaldehyde used in concentration 5 mL of 5% formaldehyde and 95 mL water, and the test #2 injectant was the formaldehyde-$H_2O_2$ combination used in concentrations as 50 mL water plus 5 mL of 5% formaldehyde plus 10 mL of 7 ppm hydrogen peroxide.

FIG. 16 provides testing conditions for formaldehyde and hydrogen peroxide combination ($CHOH/H_2O_2$) catalysis reactions using three different test substrates. The read-out was the measured pH of the test section effluent before and after injection of the $CHOH/H_2O_2$ combination. The injectant was a formaldehyde-$H_2O_2$ combination used in concentrations 50 mL water plus 5 mL of 15% formaldehyde plus 10 mL of 7 ppm hydrogen peroxide. The injection rate was 50 ccpm. Two flow rates (including a low flow rate, LF) were tested.

FIG. 17 provides as table with hydrogen peroxide catalysis reaction conditions using three different substrates, namely, stainless steel rod, abraded stainless steel with 0.01 $\mu g/cm^2$ platinum, and platinum foil flag. Each of the reactions used 3.5 ppm $H_2O_2$ injection at a flow rate of 5 ccpm at two different high temperatures.

FIG. 18 provides a table with the results of hydrogen peroxide survival fraction analysis following exposure of hydrogen peroxide to three different substrates, which were untreated stainless steel rod, abraded stainless steel with 0.1 $\mu g/cm^2$ platinum, and platinum foil. Results from reactions conducted at 125° C. and 150° C. are provided.

FIG. 19 provides various chemical reactions of relevance to the present disclosure. The reactants and the reaction products are shown.

DETAILED DESCRIPTION OF THE INVENTION

Figure 1:
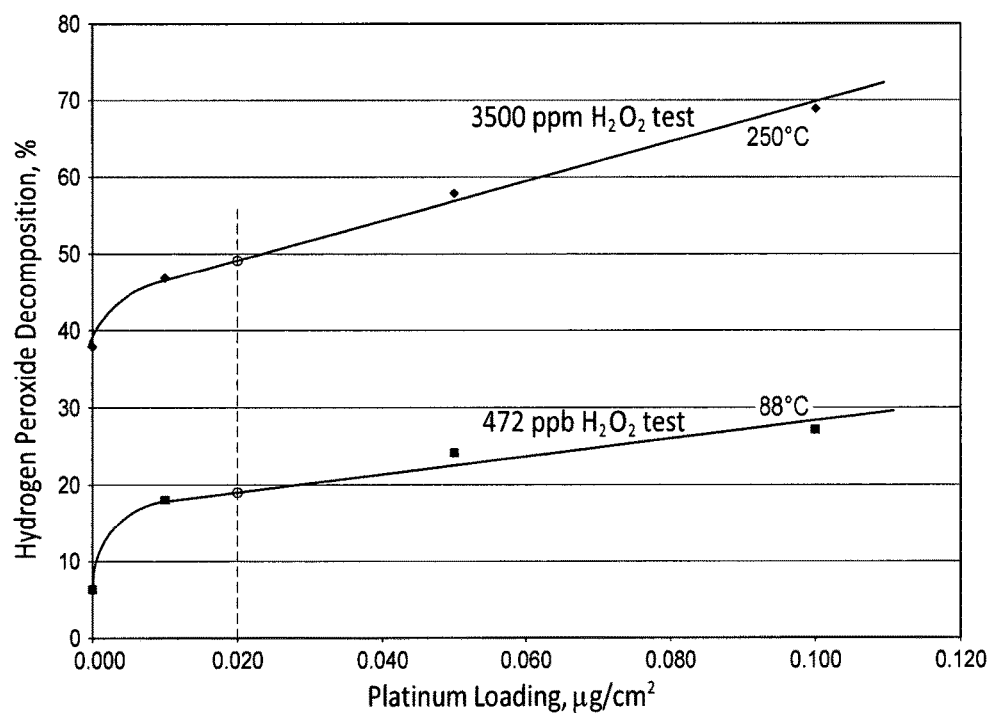
FIG. 1 provides a graph showing the hydrogen peroxide decomposition (in percentage) as a function of platinum loading ($\mu g/cm^2$) in two different reaction conditions, namely, varying the temperature (88° C. and 250° C.) and $H_2O_2$ concentration (472 ppb and 3500 ppm).

Operators of boiling water reactors have strived to mitigate stress corrosion cracking (SCC) in reactor internal components, and in particular, in the stainless steel piping, welds and reactor vessel internals of BWRs. Chemical mitigation technologies such as noble metal chemical application (NMCA) and on-line NMCA (OLNC) have alleviated some of the SCC issues in BWR components. NMCA and OLNC methods can apply a layer of platinum to a solid surface, such as stainless steel to reduce SCC in reactor components.

Quantitative assessment of the levels of platinum that have been loaded onto a stainless steel surface (or remain on the surface after a period of plant operation) is a critical metric in the monitoring of reactor plant integrity and maintenance. In some aspects, the methods of the invention will greatly facilitate the process by which utilities are able to show the presence of noble metal on reactor internal surfaces to regulators to gain inspection relief. In other aspects, the methods of the invention can quantitatively assess the level of a noble metal loaded, i.e., doped, onto the surface of a substrate. Further, using the non-destructive assay techniques of the invention, the utilities can decide whether or not (or when, e.g., how frequently) to reapply noble metal to a substrate surface by monitoring the noble metal loading values. Lower-limit threshold values in the course of monitoring the level of metal doping on the substrate surface can indicate a need to reapply noble metal to the substrate surface. This latter benefit will be most applicable to plants that do not apply noble metals annually to the reactor surfaces.

These methods of the invention provide advantages over the state of the art. The methods of the invention do not require the destructive removal of any metal oxide removal, do not use aqua regia sample digestion, and do not require expensive instrumentation such as inductively coupled plasma mass spectrometry (ICPMS) analysis for analysis of the noble metal. The methods of the invention can be used at BWR plants during each noble metal chemical application (NMCA) or on-line noble metal chemical application (OLNC) as part of a monitoring program. Furthermore, the methods of the invention can be adapted as in situ tools for evaluation of catalytic effectiveness of reactor internal surfaces. These methods of the invention can also be adapted for use in pressurized water reactor (PWR) systems in addition to boiling water reactor (BWR) systems.

The invention provides rapid, non-destructive approaches to determining the noble metal loading, e.g., platinum loading, on a substrate surface such as a stainless steel surface, where the methods are distinctly different from the destructive traditional approach known in the art.

As used herein, the expression "deposited noble metal on a substrate surface" or similar or equivalent expressions refer to noble metal deposited on the outer layer of the substrate oxide surface.

As used herein, the expressions "surface doping" or "a doped surface" or "doped substrate" or similar expressions refer to noble metal incorporated in the substrate oxide, not just on the outer surface layer.

In its broadest aspect, the invention provides a variety of methods for assessing the presence or absence of a noble metal on a surface. i.e., the method is used qualitatively. In other preferred embodiments, the methods of the invention allow the quantitative assessment of noble metal loading on the surface of a substrate, such as stainless steel. In some embodiments, the noble metal that is assayed is platinum.

In one aspect, the invention provides novel methods for the validation and quantitation of noble metal loading on substrate surfaces, such as on the stainless steel components of BWR reactor internal surfaces. The methods of the invention are readily adapted for the qualitative or quantitative assessment of platinum metal loading on stainless steel surfaces. When the techniques of the invention are used quantitatively to measure noble metal loading, the noble metal loading assessment incorporates a calibration step where control substrate samples containing known metal loading values are analyzed in parallel with the experimental samples, thereby constructing a standard curve against which the experimental samples can be compared.

The non-destructive approach of the invention can be deployed in an in situ materials monitoring system (MMS), or can be used in an ex situ context that can be performed in the plant's radiation laboratory with a removed MMS section. No sample cutting, stripping or digestion in aqua regia is needed, and the stainless steel section can optionally be reinstalled in the MMS for periodic analysis since this is a non-destructive technique.

Methodology

The invention is directed to methods for the non-destructive validation and quantitation of noble metal loading on materials surfaces. These methods utilize the catalytic reactivity of noble metals that are deposited onto a substrate surface to decompose a redox active species, such as but not limited to hydrogen peroxide or formaldehyde, in order to qualitatively assess the presence or absence of a noble metal on the surface of a substrate. Alternatively, the method is used quantitatively to measure the quantity of a noble metal that is loaded onto the substrate surface.

In the presence of a noble metal, the redox active species, e.g., hydrogen peroxide, is decomposed by the catalytic reactivity provided by the noble metal, e.g., platinum. Initially, the substrate surface to be tested is exposed to a solution containing the redox reagent in a known concentration. The exposure of the redox reagent to the noble metal deposited on the surface of a substrate results in the catalysis and reduction in concentration of the redox reagent. The decomposition and reduced concentration of the redox active species can be measured by any suitable method, and can be monitored directly or indirectly. The monitoring can be in real-time, or taken at a single time point following a reaction for a fixed time interval, and typically at a fixed temperature.

Techniques for measuring the decomposition of a redox reagent, e.g., hydrogen peroxide, are well known and readily utilized with the present invention. It is not intended that the invention be limited to any one particular method for assaying the concentration of the redox active species used in the reactions.

The amount of metal, e.g., platinum, loaded onto the surface of the sample is assayed by measuring the surface reactivity of the sample, i.e., the catalytic activity of the surface to be measured. For example, platinum can promote the redox degradation of hydrogen peroxide to produce oxygen gas. Exposure of the deposited platinum on a sample surface with hydrogen peroxide results in decomposition of the hydrogen peroxide to a degree that is directly proportional to the amount of platinum that is present. By contacting the platinum-containing sample to a fixed concentration of hydrogen peroxide, for a fixed amount of time, at a fixed temperature, the degradative oxidation of the hydrogen peroxide can be monitored by measuring the loss of hydrogen peroxide following the controlled reaction. Optionally, by the use of calibration standards, for example as provided in FIG. 1, the degradation of hydrogen peroxide in the reaction is a direct measure of the platinum loading on the surface of the sample. It is a particular advantage of this particular assay system that the levels of hydrogen peroxide in solution can be easily and rapidly measured with a handheld meter without the use of sophisticated instrumentation.

Qualitative Analysis

In some aspects, a simple qualitative application of the methods of the invention is sufficient to simply determine the presence or absence of a noble metal on the substrate surface. Using the methods described herein, a substantial reduction in the concentration of the redox reagent when in the presence of the substrate surface being tested indicates the presence of a noble metal on the substrate surface. In some embodiments, this reduction is experimentally reproducible and statistically significant.

As used herein, the substantial reduction in the concentration of the redox reagent can include a reduction of at least 50% of the starting concentration of the redox agent, at least 60% (i.e., a 40% survival fraction), at least 70% (i.e., a 30% survival fraction), at least 75% reduction, at least 80% reduction, at least 85% reduction, at least 90% reduction, at least 95% reduction (i.e., a 5% survival fraction) or substantially all of the starting redox reagent (essentially no detectable redox agent survives).

In some embodiments of this method, one or more suitable reference samples containing no added noble metal are analyzed in parallel with the experimental sample(s).

Quantitative Analysis

In some aspects, a quantitative analysis (in contrast to a qualitative analysis) is preferred where the actual noble metal loading value of an experimental substrate surface is determined. In these embodiments, the methods of the invention entail constructing of series of reference standards, also termed calibration standards, that can be used to ascribe a known metal loading value to an experimental measurement of an unknown sample. As described herein, reference standards comprising samples of stainless steel that have been precoated or deposited with known surface load concentrations of platinum can be used. These reference standards are used to construct a "standard curve" or "calibration curve" of known metal loading values (e.g., see FIG. 1) that can be used in the assessment of unknown experimental samples, where the results using the experimental samples are compared to the results of the calibration samples in order to assign a loading value to the experimental sample.

Stainless steel (stainless steel) surfaces with known platinum loadings were created using Faraday's law by electrodepositing platinum onto stainless steel surfaces from a chloroplatinic acid ($H_2PtCl_6 \cdot 6H_2O$) chemical solution using a constant current over a known period of time. The platinum loading can be calculated from the number of coulombs passed during the electrodeposition process using the equation:

$$m_{Pt} = [195 \times Q/4F].$$

In this equation, $m_{Pt}$ is the mass of platinum in grams, Q is the number of coulombs used during the electrodeposition process and F is the Faraday constant. This approach allowed the deposition of very low loadings of platinum on stainless steel surfaces that are hard to measure by the digestion and ICPMS analysis approach because the resulting platinum concentrations can be below the detection limit of the ICPMS instrument.

The platinum-treated surface was then used to test the catalytic activity by using a number of oxidation/reduction reaction systems. Initial tests were performed at 60° C. to 90° C. to select an optimal redox system appropriate for further testing. Additional tests were carried out at higher temperatures (125° to 250° C.), where the catalytic activity is more potent. Preoxidation of stainless steel rods was performed at 275° C. in air saturated water (8 ppm $O_2$) over a 21 day period.

The platinum-treated stainless steel surfaces were alternatively tested for their catalytic activity in methanol ($CH_3OH$), formaldehyde (HCHO) and hydrogen peroxide ($H_2O_2$). In some cases, a combination of the above species and $H_2O_2$ was also used. The catalytic activity was measured either by a pH change (HCHO) or by measuring the decomposition of $H_2O_2$.

The preliminary testing with $CH_3OH$ was not successful since the oxidation of methanol on platinum is a difficult process. Testing with HCHO and $H_2O_2$ showed partial success in high temperature tests. Testing with $H_2O_2$ was successful both at elevated temperature and high temperature. Based on this preliminary testing, systems that use the decomposition of $H_2O_2$ were selected for development, as it was demonstrated that this system can be used effectively to establish a correlation between the platinum loading and the catalytic activity by monitoring the $H_2O_2$ survival fraction.

Generally, the method involves exposing the platinum-treated stainless steel surface to a solution of $H_2O_2$ of known concentration at the selected temperature, allowing $H_2O_2$ decomposition to occur over a period of time and then measuring the remaining $H_2O_2$ content in the solution using a simple $H_2O_2$ analyzer. The amount of $H_2O_2$ decomposed is a function of the catalytic activity at a given temperature. Since the amount of platinum deposited on the surface is known from the number of coulombs passed from Faraday's law calculations, the decomposed $H_2O_2$ content can be correlated to the platinum loading or the catalytic activity.

FIG. 1 provides a plot showing the $H_2O_2$ decomposition (measured as percentage) as a function of the platinum loading ($\mu g/cm^2$) on the stainless steel surface, under two different defined reaction conditions. These reaction conditions used, alternatively, a lower temperature case and the higher temperature case, and under two different defined $H_2O_2$ starting concentrations (472 ppb and 3500 ppm). This figure clearly illustrates that once the $H_2O_2$ decomposition percentage is known, the platinum loading on the surface can be calculated from the plots. As an example, the broken vertical line in FIG. 1 shows that if the $H_2O_2$ decomposition test was done at 250° C. and if the percentage decomposition is 48%, then the platinum loading on the surface is 0.02 $\mu g/cm^2$. Similarly, if the decomposition test was done at 88° C., and if the percentage decomposition is 18%, then the platinum loading on the surface is 0.02 $\mu g/cm^2$. It is important to note that the tests at each temperature must be done with the same starting $H_2O_2$ concentration and the test period has to be the same in all tests in order to obtain accurate platinum loading data.

Testing Apparatus

Figure 2:
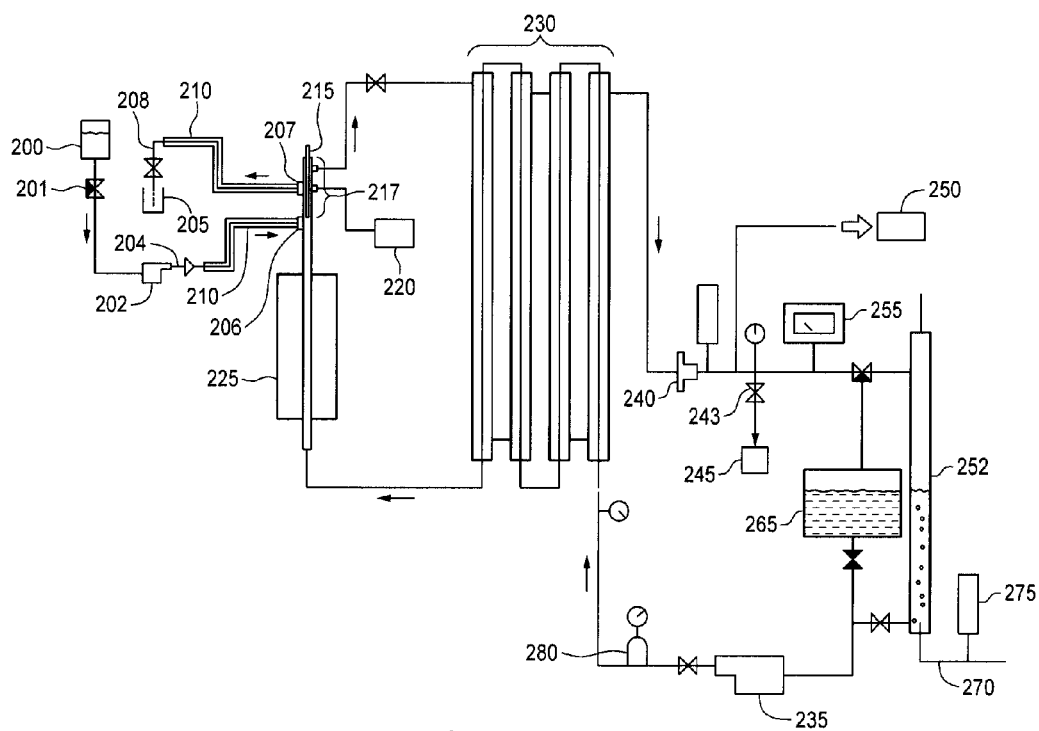
FIG. 2 provides a schematic illustration of a loop configured for high temperature catalysis injection testing.

FIG. 2 shows a general schematic of a high temperature flow loop apparatus that was used to generate the high temperature $H_2O_2$ decomposition testing data. The apparatus shown in FIG. 2 is discussed in further detail in EXAMPLE 7. The $H_2O_2$ solution injection point 206 and the reacted $H_2O_2$ solution collection point 207 are labeled. In the schematic shown in FIG. 2, the test specimen is a stainless steel rod 215, where the bottom one inch of the rod had been previously deposited with platinum. The portion of the rod 215 and apparatus where the surface catalytic activity of the tested material, i.e., noble metal reactivity, is monitored is termed generally the "test section" 217.

An $H_2O_2$ injection pump 202 is used to deliver $H_2O_2$ solution from a $H_2O_2$ reservoir 200 into the test section 217 at the $H_2O_2$ solution injection point 206. After the $H_2O_2$ solution is exposed to the catalytic surface of the stainless steel rod 215 test material, a reacted $H_2O_2$ solution sample 205 is removed at a collection point 207.

Figure 8A:
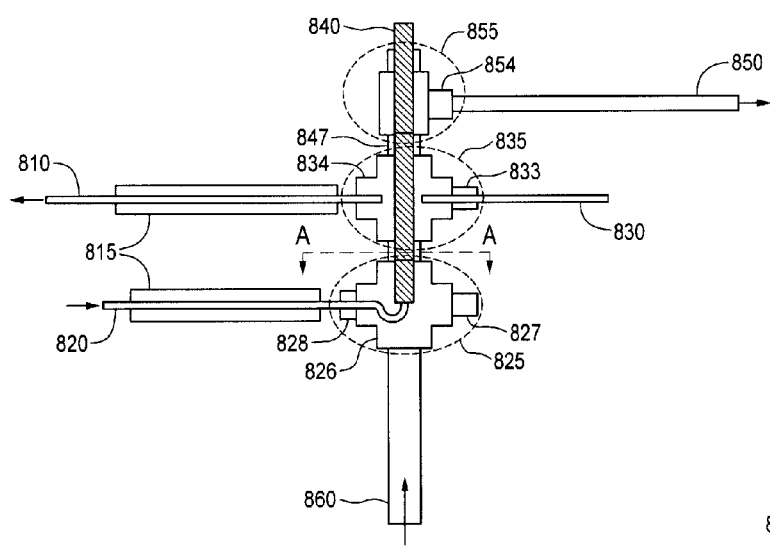
FIGS. 8A and 8B provide a detailed expanded schematics of a test section showing the injection and sampling lines of the apparatus of FIG. 2.
Figure 8B:
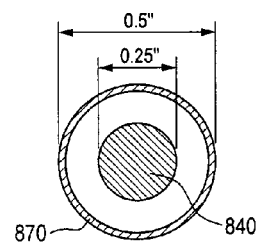

Further details of the test section 217 and test specimen rod 215 are shown in FIGS. 8A and 8B, and discussed in EXAMPLE 7.

For low temperature testing, the catalytic surface of the stainless steel rod 215 is immersed in a beaker containing the appropriate concentration of $H_2O_2$ solution. The beaker is placed on a stirrer/hotplate to achieve the desired temperature.

Noble Metals

The methods of the invention are broadly applicable to the analysis of loading of metals onto substrate surfaces, for example, the noble metals ruthenium (Ru), rhodium (Rh), palladium (Pd), silver (Ag), osmium (Os), iridium (Ir), platinum (Pt), gold (Au), mercury (Hg), rhenium (Re) and copper (Cu). The methods of the invention find use with any metals that show catalytic activity towards a redox molecule such as hydrogen peroxide. The Examples provided herein analyze the surface loading of platinum. However, it is not intended that the methods of the invention be limited to the surface loading analysis of platinum.

For example, the metals rhodium, platinum and palladium are used to load the surfaces of stainless steel or ceramic matrices, for example, in the automotive catalytic converter industry for the purpose of reducing exhaust gas emissions. The NMCA/OLNC techniques can be used to apply these metals to substrate surfaces.

Also for example, the metals platinum and rhodium are used to load the surfaces of ceramics, metals or zeolites for the purpose of petroleum production.

As with platinum, the methods of the invention can be used to analyze the surface loading of each of these metals.

Metal-Loaded Substrates

The invention provides methods for the analysis of surface loading of metals onto substrate surfaces. The substrate that contains the metal-loaded surface is not particularly limited. The Examples herein describe the use of stainless steel substrate that contains a surface upon which is deposited platinum. However, it is not intended that the invention be limited to methods for the analysis of surface noble metal loading on stainless steel, as a wide variety of substrates can be used in the analysis for surface metal loading. Other substrates that can be used include non-metals such as porous ceramic matrices, zeolites, carbon based materials and porous metals.

The substrate surfaces to be analyzed by the methods of the invention can be any suitable substrate surface that has been loaded with a surface metal. In some aspects, the substrate is a rigid substrate, for example, a metal substrate such as stainless steel (which has been loaded with a surface metal treatment). When the substrate is a metal substrate, the metal can be oxidized so that the noble metal can be incorporated in the oxide matrix in addition to the surface of the stainless steel. However, rigid substrates in addition to stainless steels also find use with the invention. Indeed, any substrate that can be a target for surface loading finds use with the invention. For example, in the nuclear industry, any materials that are used to construct reactor internal components find use with the invention, regardless of whether they are stainless steel or non-stainless steel, and regardless of whether they are metal or non-metal. For example, substrate materials such as porous ceramic matrices, zeolites, porous carbon and porous metals are also contemplated and find use with the invention.

In some aspects, the substrate under analysis is non-rigid, i.e., it is flexible. For example, flexible substrates can include carbon nanotubes, flexible polymers and plastics that can be used in non-nuclear industries.

As used herein, the term "flexible" refers to materials that undergo dimensional changes when a tensile or a compressive force is applied on the material. Examples are carbon nanotubes, flexible polymers, rubbers and plastics.

As used herein, the term "rigid" refers to materials that do not undergo dimensional changes with the application of a tensile or a compressive force, but may undergo brittle fracture, if excessive force is applied. Examples are ceramics, zeolites, non-flexible hard plastics.

The substrate surfaces to be assayed are generally rigid substrates that have been coated with a noble metal such as platinum over a surface of defined area, where the surface area is known, or can be ascertained. For example, the surface that is to be analyzed can be an interior surface of a portion of a pipe, where the surface area is $A=2\pi rh$, where A is the surface area of the interior of the pipe, r is the internal radius of the pipe, and h is the height (or length) of the pipe.

When a substrate (such as a portion of a metal pipe or a metal fragment) is being analyzed for surface loading value, it is generally only one surface that is potentially loaded with the noble metal.

Redox Active Molecules

The invention provides methods for the analysis of surface loading of metals such as noble metals onto substrate surfaces, where the methods use redox active molecules to identify and quantitate catalytically active metals/materials on the substrate surface. The Examples herein describe the testing and use of, alternatively, hydrogen peroxide and combinations of hydrogen peroxide with formaldehyde in the assay of surface-loaded metals.

As used herein, the expression "redox active molecule" refers to any species that can undergo oxidation or reduction in the presence of a catalyst. Hydrogen peroxide is just one example of a redox active molecule, but the terminology can apply to any species that can be oxidized or reduced.

However, it is not intended that the invention be limited to the use of hydrogen peroxide or formaldehyde in the assessment of catalytic activity on the surface of a substrate for the purpose of ascertaining surface loading of metals. The use of additional alternative redox-active molecules are contemplated, for example, any aldehyde that can be oxidized to an organic acid, any organic acid that can be reduced to an aldehyde or ultimately to an alcohol, for example acetic acid, can be reduced to acetaldehyde and then to ethanol, and reduction of hydrogen ion from acids to gaseous hydrogen can potentially find use with the methods of the invention.

Ideally, for whatever redox reagent is used, the redox change of that molecule can be easily and rapidly measured without the use of sophisticated instrumentation. For example, the decomposition of hydrogen peroxide can be easily monitored, alternatively, by colorimetric methods with commercially available simple instruments, by oxygen gas measurements, or by using amperometric techniques. The oxidation of formaldehyde can be easily monitored by using a conductivity measurement, pH measurement, or by using infrared spectroscopy.

Reaction Conditions

The methods of the invention can be utilized in a broad range of temperatures, pressures, reaction times and reagent concentrations. It is not intended that any of these variables be limiting. One of skill in the art will recognize that the reaction conditions described herein can be adapted and modified in the hands of any given user, using the present disclosure for guidance. It is intended that such routine modification falls within the scope of the present invention. A user of the invention will know to adapt the reaction variables described herein for the purpose of routine optimization, taking into account their own experimental preferences, equipment restraints, the nature of the materials to be tested, or other system limitations. Thus, reaction conditions that may not be specifically recited in the present application are also intended to be within the scope of the claimed invention.

For example, the methods of the invention are operative in a wide range of temperatures, for example, in a temperature range of 25° C. to 320° C., inclusive of those terminal values. In some embodiments, the methods of the invention are practiced in the range 50° C. to 320° C., inclusive of those values, having the advantage of better catalytic activity and faster results. This is because at lower temperatures, the catalytic activity is lower. At temperatures greater than 100° C., pressurized high temperature systems such as but not limited to those shown in FIG. 2 or FIG. 7, or similar configurations, would be necessary to conduct the testing, as would be recognized by one of skill in the art.

More broadly, any apparatus of the invention can have the same or similar functional elements as shown in FIG. 2. One of skill in the art will recognize that an apparatus of the invention can include elements that are not identical, but are functionally equivalent to elements shown in FIG. 2, and where the apparatus remains within the scope of the presently claimed invention. This is particularly true in the scenario that the apparatus depicted in FIG. 2 is optimized or modified for portability, ease of use, size reduction, adaptation to any given site of use, for example a BWR plant, and/or optimized for commercial sale.

Still other suitable temperature ranges are contemplated, based on optimization of any given set of reaction conditions. For example, other contemplated temperature ranges (alternatively inclusive or exclusive of the terminal bracketing values) include but are not limited to temperatures above about 100° C., temperatures of about 40° C. to 80° C., 125° C. to 150° C., and 200° C. to 320° C.

The pressure or pressure ranges used in the methods of the invention are dependent on the temperatures that are used. The pressures used needs to be maintained above the equilibrium vapor pressure of water at that given temperature to prevent boiling. As an example, at 320° C. the equilibrium pressure is 112.84 bars (1636 psi). Therefore, if a test is conducted at 320° C., the system pressure has to be maintained above 1636 psi.

Figure 11:
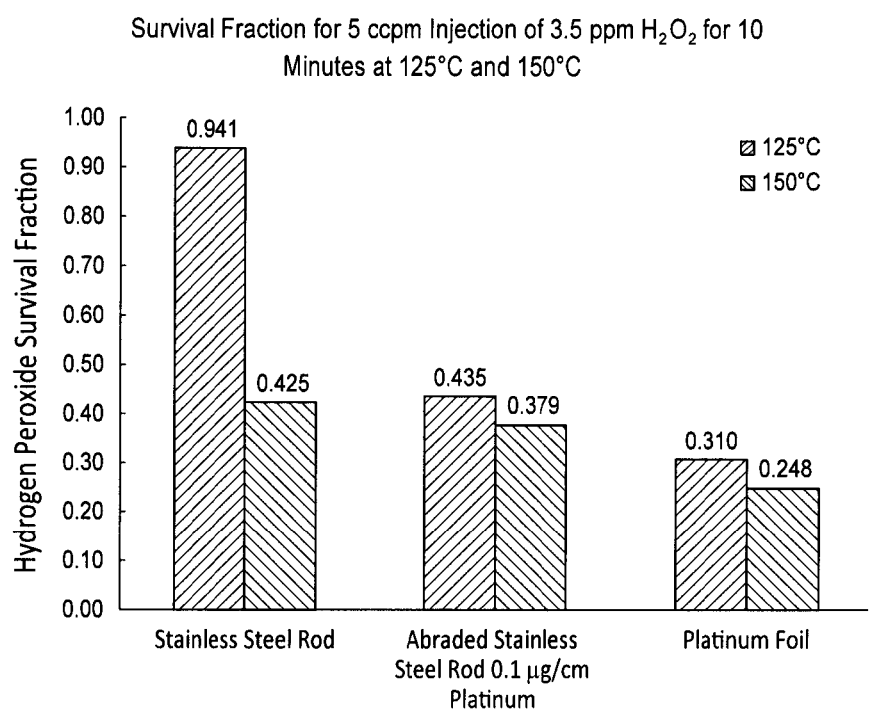
FIG. 11 provides histogram data measuring $H_2O_2$ survival fraction of 3.5 ppm hydrogen peroxide injection at 5 ccpm in three different samples, tested in two different temperatures, 125° C. and 150° C.

Reaction times, i.e., the redox reaction times, used in the methods of the invention are variable, and depend in part on the $H_2O_2$ concentration and on the temperature that are used. At lower temperatures, lower $H_2O_2$ concentrations can be used over longer periods of times. At higher temperatures, since the catalysis is faster, the reaction times can be shorter. Therefore, in order to complete the tests over a reasonable period of time, a higher $H_2O_2$ concentration may have to be used. As an example, at temperatures of 40° C. to 80° C., a concentration of 400 ppb $H_2O_2$ can be used over a reaction time of approximately 30 minutes to one hour to get a reasonable degree of decomposition of $H_2O_2$ that is measurable with a simple hand-held commercial colorimeter. At higher temperatures like 200° C. to 320° C., higher concentrations of $H_2O_2$ in the range of several to many ppm range would be needed to have a measurable quantity of $H_2O_2$ remaining after decomposition. This issue is illustrated in FIG. 11 where 3.5 ppm $H_2O_2$ solution injection was used in tests conducted in the temperature range 125° C. to 150° C. to complete the tests within a reaction time of approximately 10 minutes.

Nuclear Reactor Monitoring

As described further herein, the methods of the invention are adaptable to assess the noble metal loading of surfaces in the context of nuclear reactor internal components. The methods of the invention can be customized with various degrees of automation for use in monitoring nuclear reactor surfaces. As described herein, the methods can take the form of an ex situ material monitoring system (MMS), where the surfaces to be analyzed for metal loading can be, for example, pipes or chambers that are connected to the reactor system, but can be isolated and easily removed for monitoring purposes, as shown in FIG. 4. Alternatively, as described herein, the methods can take the form of an in situ material monitoring system, where the surfaces to be analyzed for metal loading remain intact (in situ), and the reagents that are used to determine metal loading flow over the surface to be analyzed, and the catalytic activity of the surface is analyzed "in line" from the flow stream without the need to remove and isolate the material monitoring system components. This in situ arrangement is shown in FIG. 3.

In Situ Material Monitoring Systems

Figure 3:
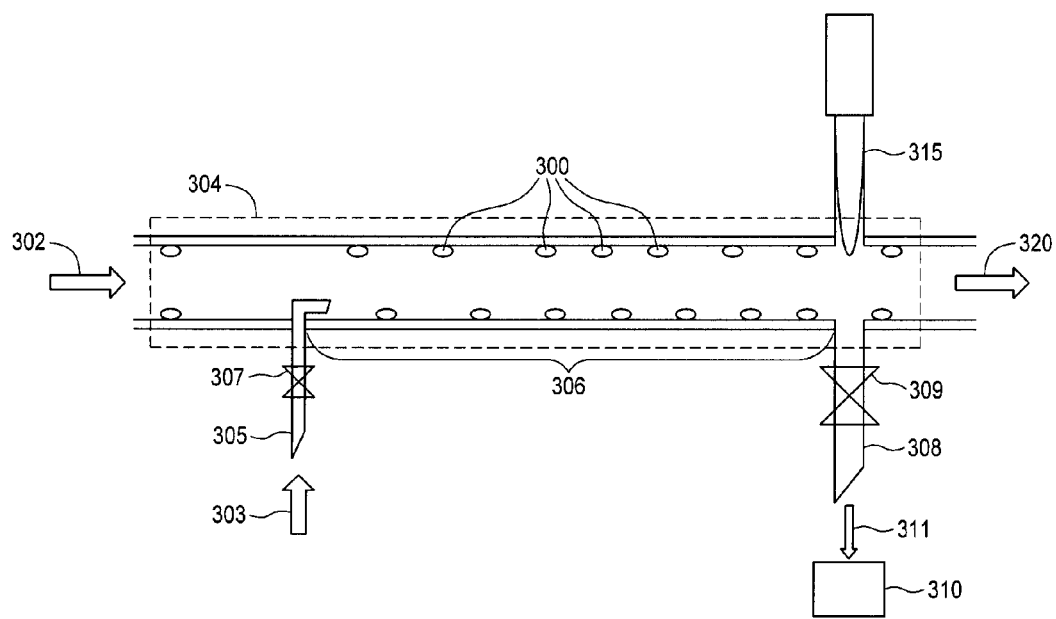
FIG. 3 provides a schematic illustrating an in situ material monitoring system for monitoring noble metal catalytic activity associated with the walls of a liquid flow channel, as might be utilized in a BWR plant application.
Figure 4:
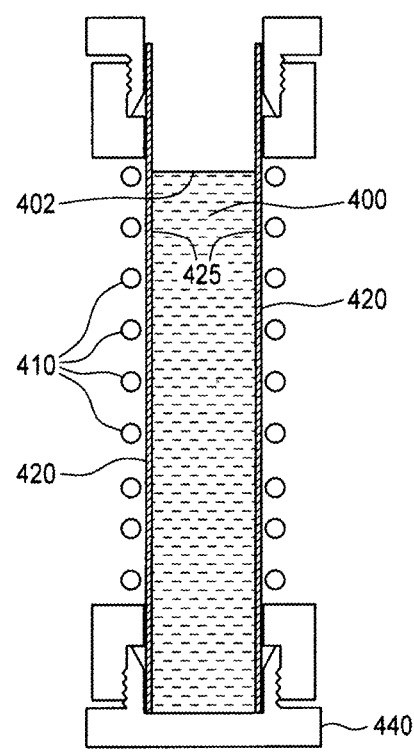
FIG. 4 provides a schematic illustrating an ex situ material monitoring system for monitoring noble metal catalytic activity associated with the walls of an OLNC-treated monitoring chamber section, as might be utilized in a BWR plant radiation laboratory.
Figure 5:
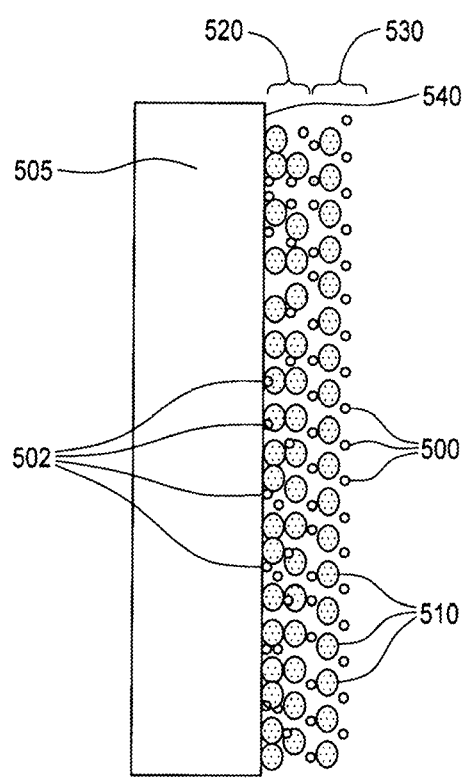
FIG. 5 provides a schematic of a platinum loaded oxidized stainless steel surface treated by OLNC.

FIG. 3 provides a schematic of an in situ catalytic activity measurement approach for a material monitoring system, also termed a "flow system," for use in operational BWR plants. This approach is based on the same theory as the 250° C. testing conducted in the laboratory. In an operating BWR plant, the decomposition test can be performed on-line, if necessary, at temperature using the configuration generally shown in schematic of FIG. 3. Water from a BWR indicated by an arrow 302 on the left of the figure can be continuously channeled through an in situ material monitoring system (MMS) in the direction of the arrow 302, where the MMS is contiguous with the reaction chamber, for example, where the material monitoring system comprises a conduit 304, such as any suitable tubing, pipe, hose, channel or the like, which can be rigid or flexible, through which the reactor water flows in the direction indicated by the arrow 302. The conduit or channel 304 is preferably made of the same materials as the BWR reactor chamber, for example, stainless steel.

Within the channel 304, there are installed at least two access ports. At one end is an injection port 305 in combination with a suitable valve 307 upstream of the catalytic surface test section 306 to be analyzed for noble metal deposition. Indicated by arrow 303, $H_2O_2$ or any suitable detection reagent can be delivered to the BWR liquid flow 302 passing through the channel 304 through the injection port 305. At a distal point downstream of the injection port 305 and further downstream of the catalytic surface test section 306, the liquid flow can be continuously monitored, or alternatively, can be periodically sampled using a sampling port 308 in combination with a suitable valve 309. Through this sampling port 308, a liquid sample 310 can be removed from the liquid flow for analysis, indicated by the arrow 311. The surface area within the channel bounded by the injection port 305 and the sampling port 308 is termed the material monitoring system test section 306. It is in this test section 306 that the surface catalytic activity with regard to noble metal reactivity is monitored.

In the in situ testing approach shown in FIG. 3, reactor water 302 enters the monitoring channel 304 with a left-to-right direction of flow indicated by the arrow 302 at the far left. A suitable monitoring reagent 303 (e.g., a redox active reagent such as $H_2O_2$) at a known starting concentration is delivered into the reactor water stream through the injection port 305 that is upstream of the catalytic material monitoring system test section 306. The injected indicator reagent results in a detectable feature that indicates the presence or absence of catalytically active noble metal (e.g., platinum 300) on or associated with the inner surface of the test section 306. For example, a suitable indicator reagent can be a reagent that creates a redox potential change, a conductivity change, a pH change, a change in concentration of the indicator species added, a detectable chemical conversion such as degradation of the starting reagent or generation of a new detectable product by way of chemical conversion, or a colorimetric change, or any other type of measurable change that correlates with the presence of catalytically active noble metal.

For example, hydrogen peroxide and/or formaldehyde find use as indicator reagents for the presence of noble metal such as platinum, because in the presence of catalytically active platinum 300 on the surface of the test section wall 306, the indicator reagent (e.g., hydrogen peroxide) will decompose, resulting in a measurable reduction in the concentration of the hydrogen peroxide as it travels through the test section flow stream 306 downstream of the injection port 305 until it reaches the sampling port 308 or passes a suitable in situ sensor.

Thus, there is a readily detectable decrease in the concentration of the hydrogen peroxide that is added, and that decrease is due to the presence of deposited noble metal. In the case of hydrogen peroxide, the concentration of that species in the flow stream can be rapidly assessed using widely available and inexpensive instrumentation. Determination of catalytic activity of the test section surface is assayed by detecting (or measuring) the extent of the reaction between the injected chemical monitoring reagent and the catalytic surface.

As illustrated in FIG. 3, the testing of the flow can be performed by one of two methods (or using both methods). First, testing of the flow can be accomplished by withdrawing (indicated by arrow 311) a liquid sample 310 through a sampling port 308 controlled by a suitable valve 309 for further analysis. Second, testing can be done in real-time using sensors installed downstream of the catalytic test section 306 and embedded within the material monitoring system structure.

Sensors that are embedded within the material monitoring system structure can be any suitable sensor type that measures (directly or indirectly) the concentration of an indicator reagent passing through the material monitoring system. FIG. 3 shows the use of a reference electrode 315, the tip of which contacts the flow stream so that the electrochemical corrosion potential (ECP) of the flow channel 306 can be monitored if the liquid stream 302 entering the flow channel has excess hydrogen so that the molar ratio of $H_2/O_2$ is greater than 2. Under these conditions, the ECP of the flow channel 306 is expected to be very low, reaching values close to $-500$ mV(SHE) because of the catalytic activity of the channel 306. This is an approach to prove the presence of noble metal on the surface of the flow channel 306. In this particular scenario, no chemical injection through the port 305 is required.

In the case of $H_2O_2$, decomposition of that molecule reflects the catalytic activity of the inner wall of the test section 306, and is quantitated by measuring the remaining $H_2O_2$ reagent in the flow stream (i.e., the survival fraction) in the material monitoring system channel that flows to the downstream sampling port 308 or an in situ sensor 315. The arrow 320 on the far right in FIG. 3 indicates the reactor water flow stream exiting the material monitoring system channel 304, directed towards a reactor water clean up (RWCU) system.

Ex Situ Material Monitoring Systems

In contrast to an in situ material monitoring system (MMS), the methods of the invention can be adapted for use in an ex situ material monitoring system, as shown in FIG. 4, also termed a "static system." In this type of system, a section of the materials monitoring system is designed to be in contiguous contact with the reactor water environment, but is also designed to be removable from the reactor environment so that it can be physically removed to permit analysis of noble metal deposition on the exposed surface of that component. In various aspects, that removable component can be any form, such as but not limited to, a portion of a pipe, tube, channel or segment of any type. In some embodiments, the removable component is a portion of stainless steel tubing that was contiguous with the reactor environment that would have received noble metal deposition during the time that the reactor plant was subjected to noble metal chemical addition (NMCA) or on-line noble metal chemical application (OLNC). Ideally, no cutting or destructive removal of the component to be tested (such as a portion of a pipe or tube) is necessary if the section is designed to be a removable component of the monitoring system.

In some embodiments, the removable portion can advantageously contain end portion features that facilitate its installation and removal from the plant materials monitoring system and also facilitate the downstream testing for noble metal deposition. For example, removable portions that have end threading or have one or two sealable ends or are readily attachable to other apparatus or equipment find use with the invention. For example, removable portions of a material monitoring system that are adapted to be interoperable with SWAGELOK® fittings or with SWAGELOK®-type fittings find particular use with the invention. When the removed component is a tube or pipe, this feature will also allow the removed component to become a sealed system when both ends are suitably capped.

As shown in the cross section view of FIG. 4, the movable component from the material monitoring system can be tubing 420 where the noble metal catalyst to be assayed is associated with or deposited on the inner surface 425 of the tubing 420, for example, previously deposited by on-line noble metal chemical application (OLNC). The removed tubing 420 can be sealed at one or both ends by using a SWAGELOK® cap 440 that is screwed onto one end, for example, the bottom end.

The component to be assayed for noble metal deposition 420 is then filled with a suitable solution containing an appropriate marker reagent, for example, $H_2O_2$ solution 400 of known concentration and known volume. The assay system is then heated by any suitable mechanism, for example, a wound heating wire, a heating coil 410, a nichrome (nickel-chromium) coil or any other suitable mechanism, or by immersing the entire assembly shown in FIG. 4 in an elevated temperature water bath up to the level of the $H_2O_2$ 402 to achieve the desired temperature of the solution inside the tubing, for example, 88° C. or any other desired temperature. After a predetermined reaction time, for example, a sufficient time for $H_2O_2$ decomposition to occur, for example, on the order of 1-2 hours, the solution is removed, cooled and analyzed to determine the $H_2O_2$ decomposition percentage (i.e., the survival fraction) using a CHEMetrics® V-2000 multi-analyte photometer or any other suitable instrumentation that can measure the remaining $H_2O_2$, thereby indicating the platinum loading on the surface, for example, as illustrated by the standardization curves in FIG. 1. The measure of $H_2O_2$ decomposition is an indirect measure of the surface platinum catalytic activity.

In other embodiments, for example, when reagents other than $H_2O_2$ are used, the solution can be cooled and analyzed for conductivity, pH or concentration change of the chemical species that would give an indication of the catalytic activity of the surface (depending on the reaction chemistry).

This approach can be readily adopted in the radiation lab of any plant, and the surface catalytic activity of the surface or platinum loading can be determined in a few hours. Furthermore, since this is a non-destructive technique, the material monitoring system section can be reinstalled and reanalyzed periodically to determine the loss of catalytic activity over time. This approach eliminates the need to ship the MMS section to a vendor, cutting, aqua regia dissolution of the oxide, digesting or ICPMS analysis of the resulting solution, thus saving time and resources. The method provides a direct measurement of the surface catalytic activity.

The reaction temperature used for the hydrogen peroxide decomposition evaluation can be any suitable value. For example, a "low-temperature" reaction can be used having a temperature above ambient temperature and below 100° C., for example, at 88° C. Higher temperature decomposition reactions using temperatures greater than 100° C. can also be used if the open end of the assembly shown in FIG. 4 is capped and sealed, for example, with a SWAGELOK® fitting.

For in situ hydrogen peroxide decomposition and analysis of in-plant surfaces (for example, as shown in FIG. 3), the temperature is not particularly limited, for example, can be the operating temperature of the plant, during start-up, during operation or during shutdown.

Broad Industrial Applications

The methods of the invention find use in the nuclear power industry to monitor noble metal loading in nuclear reactor internal components. However, it is not intended that the methods of the invention be limited to use in nuclear plants, as the methods of the invention find broad use in any industrial setting where metals, such as noble metals, are applied to surfaces for any reason, for example but not limited to, the purpose of curtailing the effects of stress corrosion cracking.

For example, the methods of the invention find use in determining the catalytic activity of any catalytic surface. Examples include, but not limited to, automotive catalytic converters, catalysts used in oil field technology, catalysts used in recombiners, catalysts used in other industrial applications such as organic and inorganic reactions, and non-industrial applications.

Advantages

The catalytic activity testing performed with stainless steel surfaces containing known amounts of electrodeposited platinum, as described herein, demonstrate that hydrogen peroxide alone or hydrogen peroxide in combination with formaldehyde or any other suitable reagents can be used to quantitatively assess the catalytic activity of the platinum on the substrate surface in a range of temperatures, including high temperature water. Methanol was not reactive enough to provide any pH response as expected, therefore was not selected for further development as a reagent to determine the catalytic activity of noble metal treated surfaces.

The promising nature of this approach to determine the catalytic activity and/or platinum loading on plant OLNC treated stainless surfaces, without the need to cut MMS specimens, dissolve the oxide in aqua regia followed by digestion and ICPMS analysis, solves significant problems in the art, and provides additional advantages. The technique is attractive since it can be adapted to in situ or ex situ use, and can provide catalytic activity and/or platinum loading data in a relatively short time compared to the techniques that are currently in use. The technique can be employed in plants for a variety of purposes, including (a) to determine the loss of catalytic activity of plant surfaces over time and hence make a platinum reapplication decision, (b) to help achieve inspection relief criteria by satisfying the VIP-62 needs, and (c) to develop a tool to analyze accessible plant surfaces for platinum loading analysis during an outage.

Another unique feature of this technique is that since it is non-destructive, the same MMS piping or coupon section can be repeatedly used and reinstalled in the MMS after analysis for further exposure to flowing reactor water for future evaluations.

Additional aspects of the invention are further described in the non-limiting EXAMPLES, as provided below.

EXAMPLES

The following examples are offered to illustrate, but not limit, the claimed invention. It is understood that various modifications of minor nature or substitutions with substantially similar components or materials will be recognizable to persons or ordinary skill in the art, and these modifications or substitutions are encompassed within the spirit and purview of this disclosure and within the scope of the invention.

Example 1

Chemical Species Selection

An important aspect of this project was to select chemical species that can be utilized for detecting the catalytic activity of the OLNC treated surfaces. The main chemical species selected for the initial scoping tests included hydrogen peroxide ($H_2O_2$), methanol ($CH_3OH$), ethanol ($C_2H_5OH$) and formaldehyde (HCHO). These selected species were expected to undergo chemical reaction with the catalytic surface at temperature providing decomposition products that can be detected by a variety of means so that the catalytic activity can be measured. The reactions, the products and the responses expected from these reactions are listed in FIG. 19.

In the case of $H_2O_2$ reaction, either a redox potential response or decomposition of $H_2O_2$ is expected that can be conveniently measured. The amount of $H_2O_2$ decomposed would be a function of the catalytic activity. In the other three cases, $CH_3OH$, $C_2H_5OH$ and HCHO, the oxidation reactions show generation of either formic acid (HCOOH) or acetic acid ($CH_3COOH$), in either case resulting in a pH or a conductivity change. The extent of these changes would reflect the catalytic activity. This forms the basic principle behind the proposed experimental approach. These measurements can be performed by in-situ or ex-situ methodologies, as described herein.

The present disclosure provides discussion of mechanistic theories explaining how the invention works at a molecular and atomic level. However, it is not intended that the invention be limited in any regard to the chemical/molecular mechanism of action, and knowledge of such mechanisms is not required to make or use the invention. It is not intended that the expressions "degradation of hydrogen peroxide" or "loss of hydrogen peroxide" or "reduction in concentration of hydrogen peroxide" or any other equivalent or similar expression, or loss or transformation of any type of marker reagent finding use with the invention, as used herein, be limited in any way with regard to the mechanism by which the marker transformation is occurring.

Example 2

Electrodeposition of Platinum on Stainless Steel Surfaces and Loading Calculation The platinum solution needed for electrodeposition was prepared by dissolving 250 mg of chloroplatinic acid hexa hydrate ($H_2PtCl_6 \cdot 6H_2O$) in 60 ml of water. All electrodepositions were performed at room temperature. The anode used was a 0.26 mm diameter platinum wire when platinum deposition was needed on 0.2 mm diameter stainless steel wires for scoping tests. When platinum depositions were needed on ¼ inch stainless steel rods, the anode used was a platinum foil of dimensions 25 mm×5 mm×0.1 mm in order to pass a larger current. All stainless wires and rods were cleaned with isopropyl alcohol followed by a deionized water rinse before the platinum electrodeposition process.

The electrodepositions were performed by passing a constant current where the stainless steel was made the cathode and either a platinum wire or a platinum foil was used as the anode. Depending on the amount of platinum deposition needed the current applied varied from 0.01 µA to 1.5 µA. The current was measured as a voltage drop across a precision 1 MΩ or 10 MΩ resistor using a Cen-Tech voltmeter. The desired platinum loading was obtained by passing the current through the electrolyte over a predetermined period of time. The platinum loading was calculated from Faraday's law knowing the number of Coulombs passed during the electrodeposition process, using the equation shown below.

$$m_{Pt} = [195 \times Q/4F]$$

where, $m_{Pt}$ is the mass of platinum deposited, 195 is the molecular weight of platinum, Q is the charge passed during electrodeposition (usually in micro-Coulombs), F is Faraday constant, and the number 4 is the number of electrons involved in the electrodeposition process. The deposition process was assumed to have a 100% current efficiency. The mass of platinum deposited can then be converted to a loading by dividing by the surface area of the stainless steel cathode material.

Example 3

Electrochemical Measurements

Figure 6:
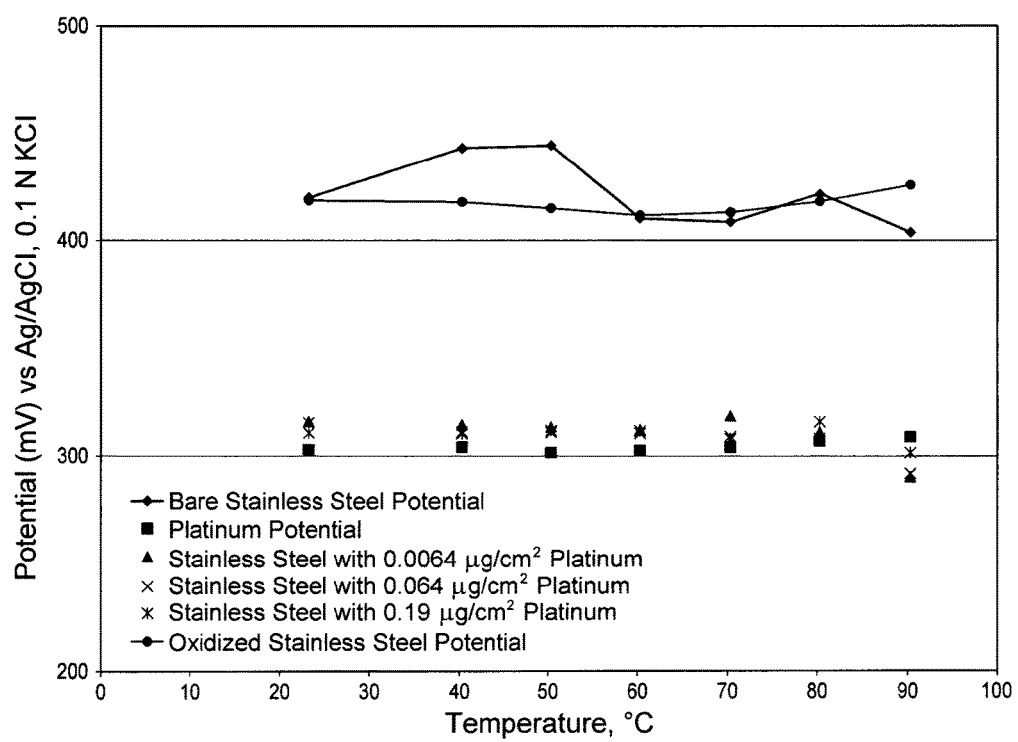
FIG. 6 provides a graph showing the potential (mV) of platinum-deposited stainless steel versus platinum-free stainless steel in 4% $H_2O_2$ aqueous solution as a function of temperature.

The potential of platinum-loaded stainless steel wire samples were monitored in 4% $H_2O_2$ solution at each temperature between 20° to 90° C. along with the potential of oxidized and unoxidized stainless steel wires for comparison. The measurements were made against an Ag/AgCl/ 0.1 N KCl reference electrode. The results are shown in FIG. 6. The plot shows that the potential of all three platinum loaded wires with loadings varying from, 0.0064, 0.064 to 0.19 µg/cm², all show potentials very close to each other. Even more revealing is the fact that pure platinum potential is also very close to the platinum loaded stainless steel potentials. Thus, it appears that stainless steel with even 0.0064 µg/cm² of platinum loading behaves electrochemically and catalytically very similar to pure platinum, showing the potency of the platinum electrodeposition process. This is consistent with a prior observation that shows that even 0.001 µg/cm² platinum is sufficient to lower the ECP of stainless steel to low values at BWR operating temperatures. Both oxidized and unoxidized platinum free stainless steel show higher potentials. It is also important to note that potential measurements are not sensitive enough to determine the amount of platinum present on the stainless steel surfaces.

Example 4

Platinum Deposit Morphology and Particle Distribution

The highly catalytic nature of the platinum deposition process is likely due to the formation of nano-particles of platinum on stainless steel surfaces. There is some evidence for this in the literature that shows the formation of platinum nano-particles on highly oriented pyrolytic graphite (HOPG) using a similar platinum deposition process; see Lu and Zangari, *Electrochimica Acta*, 51:2531-2538 (2006). It is likely that a similar nano-platinum deposit is formed on stainless steel surfaces as well. The platinum particle distribution seen in Lu and Zangari (2006) is somewhat similar to those obtained with NMCA and OLNC, except that the particle size is between those obtained with NMCA (50 to 150 nm) and OLNC (2 to 12 nm) (Hettiarachchi et al., 14th International Conference on Environmental Degradation of Materials in Nuclear Power Systems, Virginia Beach, Va., August, 2009).

Example 5

Elevated Temperature Scoping Tests with Platinum Loaded Stainless Steel Rods

This Example describes the testing of various redox reagents in the analysis of platinum deposited on stainless steel.

A) Tests with Methanol

Tests with methanol were performed with pure platinum in 300 ppm $H_2O_2$ containing 8300 ppm methanol at 82° C. over a 25 minute period with stirring to determine potential oxidation of methanol to formic acid. No change in pH was observed in the cooled liquid sample after conducting the test, indicating that the catalytic oxidation of $CH_3OH$ to formic acid did not occur on the platinum surface as anticipated. This observation is consistent with the high temperature data that also showed no detectable oxidation reaction on a stainless steel rod electrodeposited with platinum (data presented below).

Based on these observations, methanol tests with platinum loaded stainless steel samples were abandoned, in favor of the elevated temperature $H_2O_2$ tests which looked more promising.

B) Hydrogen Peroxide Decomposition Tests with Platinum Loaded Stainless Steel Wires Preliminary scoping tests were performed with three stainless steel wires of 0.2 mm diameter with platinum loadings varying from, 0.0064, 0.064 to 0.19 µg/cm², by immersing them in 4% $H_2O_2$ at temperatures of 60°, 70°, 80° and 90° C. and monitoring the extent of oxygen gas evolution due to decomposition of hydrogen peroxide on each of the stainless steel wires and comparing them with plain stainless steel with no platinum.

It was clearly visible that the stainless steel wire with the highest platinum loading showed vigorous gas evolution with less gas evolution on wires with less platinum loading. The extent of gas evolution also increased with temperature as expected. The plain stainless steel with no platinum showed little or no gas evolution. Therefore, the scoping tests and the videos obtained on oxygen gas evolution demonstrated that $H_2O_2$ decomposition on platinum deposited stainless steel can be used to measure the catalytic activity of the surface and may potentially help calculation of the surface platinum loading with proper calibration.

Hydrogen peroxide scoping tests were also performed with oxidized stainless steel in 4% $H_2O_2$ at the above temperatures after attempting to deposit platinum using the same electrodeposition technique. These were unsuccessful as evidenced by the absence of catalytic activity of oxidized stainless steel surfaces, i.e., there was no gas evolution, hence no decomposition of $H_2O_2$. Therefore, no data are reported with oxidized stainless steel surfaces. However, once the analytical technique is developed, it can be applied to oxidized stainless steel after OLNC treatment since we do know that platinum can be deposited on oxidized stainless steel by the OLNC treatment process.

C) Hydrogen Peroxide Decomposition Tests with Platinum Loaded Stainless Steel Rods—Visual Two ¼ inch diameter 3 inch long stainless steel rods were cleaned with isopropyl alcohol followed by a deionized water rinse and deposited with platinum as described in Section 2.2 in order to obtain surface platinum loadings of 0.036 μg/cm² and 0.1 μg/cm². The rods were then immersed in an aqueous solution of 4% $H_2O_2$ at 60° C. to check their catalytic activity. Both samples showed vigorous evolution of oxygen gas on their surfaces due to the decomposition of $H_2O_2$. Evolution of gas bubbles on the platinum-treated stainless steel surface was clearly evident, while very few gas bubbles appeared on the untreated stainless steel surface.

D) Hydrogen Peroxide Decomposition Tests with Platinum Loaded Stainless Steel Rods—Analytical The platinum deposited ¼ inch stainless steel rod samples having the platinum loadings of 0.036 and 0.1 μg/cm² platinum were tested along with a similar stainless steel rod with no platinum in 1000 ppm $H_2O_2$ at 80° C. over a 30 minute test period with stirring in different beakers. After the test period, the samples were allowed to cool and two series dilutions were performed to get the concentration to an analyzable range of 0 to 500 ppb. The hydrogen peroxide analyzer used was a CHEMetrics® CHEMets® K5502 hydrogen peroxide colorimetric analyzer which had a range of 0 to 500 ppb $H_2O_2$.

The results are shown in the Table provided in FIG. 12. Hydrogen peroxide survival amount is provided as $H_2O_2$ parts per billion (ppb), conducted at 80° C., comparing results for stainless steel samples with and without platinum, and two different levels of preloaded platinum. Values of 250 ppb indicates no decomposition of $H_2O_2$.

As seen clearly from FIG. 12, less $H_2O_2$ remains in solution after decomposition with stainless steel rods containing platinum, showing significant catalysis. However, the remaining $H_2O_2$ with the two loading levels of platinum are not very different even though the actual platinum loading amounts differ by a factor of three.

These values confirm that the catalytic activity of a stainless steel surface containing platinum can be monitored by using the hydrogen peroxide decomposition reaction at elevated temperature. This is evidence that the method can be adapted to estimate the catalytic activity of noble metal treated surfaces with the ultimate objective of deducing the amount of noble metal present on a stainless steel surface.

Example 6

Test Material and High Temperature Preoxidation

This Example describes the materials used in the analysis of hydrogen peroxide catalysis in the presence of platinum deposited on stainless steel.

A) Materials

The material used was 0.250 inch (5.08 mm) diameter precision ground Type 304 stainless steel meeting the requirements of ASTM A-276 and A-479. The chemical and mechanical properties of this Type-304 stainless steel heat E110333 are provided in FIG. 13.

For use in low temperature experiments, the as-received material was cut into eight 3 inch (7.6 mm) long segments to be used in low temperature tests.

For use in high temperature experiments as pre-oxidized specimens, the as-received material was cut into five 13 inch (33 cm) long segments and a divot was machined one inch (2.54 cm) from one end to set a SWAGELOK® compression ferrule at this location. The specimens were cleaned with isopropyl alcohol and de-ionized (DI) water before insertion into the preoxidation autoclave.

To prepare pre-oxidized stainless steel rods for elevated temperature testing, the stainless steel rods were pre-oxidized for 21 days at 275° C. in air saturated water at a pressure of 900 psi (6.2 Mpa). Flow rate into the autoclave was 50 cubic centimeters per minute (ccpm).

B) Test Loop

Figure 7:
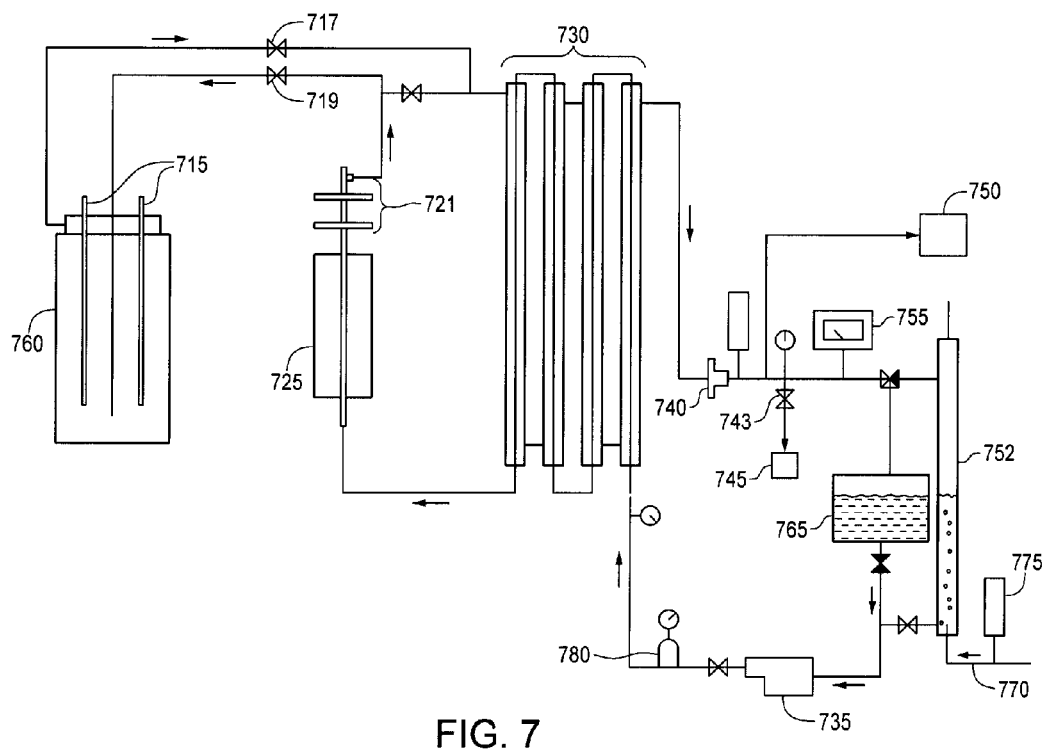
FIG. 7 provides a schematic of a high temperature test loop configured for preoxidation of stainless steel samples.

FIG. 7 shows a schematic of a high temperature stainless steel test loop that was constructed for the purpose of generating stainless steel test samples to be used in the proof-of-principle demonstrations described in the present disclosure. This figure shows the apparatus configured for preoxidation.

As illustrated in FIG. 7, the test loop has a 300 mL flow capability with a loop flow rate of 50 mL/min, and was used in conjunction with a PARKER AUTOCLAVE ENGINEERS two liter HASTELLOY® C autoclave 760 (preoxidation autoclave) with integrated heating furnace to preoxidize the stainless steel specimens. Stainless steel specimen rods 715 were preoxidized using this processing apparatus. A total of five specimen rods were generated. The preoxidation was in air-saturated water, with the autoclave temperature at 275° C.

In this process, water is drawn from a 5 gallon (19 liter) stainless steel tank 765 and pumped at high pressure by a PULSAFEEDER® PULSA Series® 680 metering pump 735 in conjunction with a pulsation dampener 780 through ¼ inch (6.35 mm) tubing into a tube-in tube regenerative heat exchanger 730 with ½ inch diameter (12.7 mm) shell side tubing. In this figure, the direction of liquid flow is indicated by arrows. The warm water flows through the test section heating tube 725 and discharges into the test section 721 during preoxidation, test sample rods are not installed in the test section 721, and the heated water simply flows through the test section 721, as there is no sample being analyzed. During decomposition testing, test sample rods are installed in the test section (see FIG. 2). The test section heating tube 725 can be used to facilitate heat-up of the preoxidation autoclave 760, but it is turned off once the autoclave has reached the desired temperature. For preoxidation purposes, the test section effluent is routed to the preoxidation autoclave 760 via a severe service valve 719. The water is introduced into the lower portion of the autoclave 760 by a down corner tube and is heated as it flows upward by the clam shell furnace surrounding the autoclave. The process temperature is maintained by a PARKER AUTOCLAVE ENGINEERS digital controller. The autoclave effluent is routed through a second severe service valve 717 to the regenerative heat exchanger 730 where it is cooled to room temperature, and then flows through an air-activated back pressure regulator 740 to maintain the desired test pressure.

The loop effluent can be directed alternatively to a cleanup system 750 or back to a gas mixing column 752. The gas mixing column 752 is used to bubble a gas from a gas source 775 connected by a gas line 770 to the bottom of the column, where the gas can be either air or some other gas of specifically defined composition as required. This gas mixing column 752 results in an air or gas equilibrated water.

The system further comprises a sampling port/valve 743 for sampling the loop effluent return water 745, if desired. An in-line conductivity meter 755 can also be used to monitor the loop effluent return water.

Further details of this system are shown in FIGS. 8A and 8B, and discussed further below.

Example 7

High Temperature Scoping Tests

This Example describes high temperature scoping tests to determine if hydrogen peroxide, methanol or formaldehyde decomposition as measured by either $H_2O_2$ survival fraction or pH changes can be employed to deduce the platinum loading on stainless steel surfaces. Successful demonstration using these protocols is affirmative proof-of-principle demonstration that it is possible to achieve the goal of determining platinum loading on OLNC treated surfaces in-situ without the need for stripping and direct analysis of dissolved oxides by inductively coupled plasma mass spectrometry (ICPMS).

Apparatus

Peroxidized stainless steel rod specimens generated as described in Example 6 using the apparatus of FIG. 7 were subjected to high temperature catalysis testing using $H_2O_2$ decomposition as a measure of noble metal-induced catalysis (i.e., noble metal reactivity). FIG. 2 shows a schematic representation of a high temperature flow loop apparatus configured for high temperature catalysis testing used to generate the $H_2O_2$ decomposition injection test data. Aspects of the apparatus shown in FIG. 2 are identical or analogous to the apparatus shown in FIG. 7 and discussed in Example 6.

FIG. 7 is the apparatus configuration used only for the preoxidation of the stainless steel specimen rods. The autoclave incorporated into this configuration is used only during preoxidation of the stainless steel rod specimens. The autoclave does not form a part of the high temperature flow loop apparatus configured for high temperature catalysis testing (FIG. 2) since the autoclave is not necessary for decomposition testing.

The configuration shown in FIG. 2 is used for decomposition testing that uses $H_2O_2$ as the redox-active species to measure catalytic activity of the test sample (i.e., stainless steel rod) surface. Arrows indicate the direction of liquid flow. Generally, the injectant $H_2O_2$ is placed in a reservoir source 200, from which it is pumped by an injection pump 202 (e.g., an Eldex Laboratories metering pump) through a feed line 204 into an $H_2O_2$ injection point 206 in the test section 217. The distance from the pump 202 to the injection port 206 is 24 inches (61 cm). A check valve 201 is installed between the pump 202 and the $H_2O_2$ reservoir 200 to prevent back flow of the fluid.

In the schematic shown in FIG. 2, the test specimen is a stainless steel rod 215 that has been installed in the test section 217, where the bottom one inch of the rod had been previously deposited with platinum.

After the $H_2O_2$ solution is exposed to the catalytic surface of the stainless steel rod 215 test material, a reacted $H_2O_2$ solution sample 205 is removed from the test section 217 through a sampling line 208, where the sampling line 208 connects to the test section 217 at the collection point 207. Cooling jacket material 210 is used to cool both the reactant feed line 204 that supplies the $H_2O_2$ injectant to the test section 217 and the sampling line 208 that is used to recover a sample of the reacted $H_2O_2$ solution from the test section 217. The extent of $H_2O_2$ decomposition in the reacted solution sample 205 was then measured. Both the reactant feed line 204 and the sampling line 208 are Teflon lined. The length of the sampling line 208 is 60 inches (1.5 meters), which is sufficient to cool the sample 205 to room temperature at a flow rate of 10 ccpm. The sampling flow rate is set by a SWAGELOK® micrometer needle valve and the flow is turned on or off with a flip top valve.

In this process, water is drawn from a stainless steel tank 265 and pumped at high pressure by a metering pump 235 in conjunction with a pulsation dampener 280 into a regenerative heat exchanger 230. The warm water from the heat exchanger 230 then flows into heating tube 225 and feeds the test section 217.

A stainless steel test sample rod 215 previously treated with noble metal is installed in the test section 217, and the preheated water from the heating tube 225 flows through the test section 217 and over the surface of the stainless steel test sample 215. The effluent from the test section is routed back to the regenerative heat exchanger 230, where it is cooled, then through an air-activated back pressure regulator 240 that maintains the desired test pressure.

The test section effluent can then be directed alternatively back to a gas mixing column 252, or to a clean-up system 250 (after which it may be returned to the gas mixing column). The gas mixing column 252 is used to bubble a gas from a gas source 275 connected by a gas line 270 to the bottom of the column, where the gas can be either air or some other gas of specifically defined composition as required. This gas mixing column 252 results in an air or gas equilibrated water. A nitrogen gas cover was maintained in the loop feed tank 265 for these tests.

The system can further comprise a sampling port/valve 243 for removing a sample 245 of the test section effluent return. An in-line conductivity meter 255 can also be used to monitor the test section return water.

For low temperature testing, the catalytic surface is immersed in a beaker containing the appropriate concentration of $H_2O_2$ solution. The beaker is placed on a stirrer/hotplate to achieve the desired temperature or in an elevated temperature water bath.

The high temperature test loop apparatus was constructed from stainless steel and had a 300 milliliter (mL) flow capability (determined by the pumps driving the system). Testing was generally conducted in the flow range of 10-100 mL/min. The test section 217 measured 3 inches (7.62 cm) in length. The stainless steel test rod specimens 215 were secured in the test section 217. Only the bottom one inch of the stainless steel rod 215 is catalytic. A thermocouple monitors the temperature of the test section 217.

Further details of the test section are provided in the views of FIGS. 8A and 8B. An expanded schematic of the test section is shown in FIG. 8A. The test section comprises two 0.5 inch (12.7 mm) SWAGELOK® crosses, termed a top cross 835 and a bottom cross 825. In addition, there is a tee-junction 855 that lies on top of the top cross 835, connected to the top cross 835 by a length of tubing 847. The three sections, namely the tee-junction 855, the top cross 835 and the bottom cross 825 are stacked upon each other such that the distance from the tee-junction 855 to the bottom cross 825, measured center-to-center, is 3 inches (7.62 cm).

The stainless steel rod test specimen 840 is introduced into the test section from the top of the tee-junction 855. The water flow enters the test section through tubing 860 connected to one branch 826 of the bottom cross 825. The direction of water flow through tubing 860 is indicated by an arrow. Water exits the test system through tubing 850 connected to one side branch 854 of the tee-junction 855, and into the heat exchanger. The direction of water flow through tubing 850 into the heat exchanger is indicated by an arrow.

Side branch 828 of the bottom cross 825 is used as an injection port to introduce the injectant solution fed by an injection feed line 820 (direction of flow indicated by arrow) into the water stream that enters the test section by the water stream feed tubing 860 connected to side branch 826. The injectant solution feed tubing 820 that used to deliver injectant solution through the injection port 828 is a stainless steel tubing with ⅛ inch (3.2 mm) inner diameter lined with Teflon (PTFE). The injection rate of the monitoring reagent solution (e.g., the $H_2O_2$ solution) through the injection line 820 is controlled by an Eldex Laboratories metering pump (see pump 202 in FIG. 2). For the purposes of these tests, one branch 827 of the bottom cross 825 is capped.

Similarly, one side branch 834 of the upper cross 835 is used as a sampling port for the extraction for samples of the water flow after the water flow has been exposed to the stainless steel rod specimen 840 surface. Sample is extracted from the port 834 through a sampling line 810 (direction of flow indicated by arrow). This sampling line 810 also uses stainless steel tubing with ⅛ inch (3.2 mm) inner diameter lined with Teflon (PTFE). Further, an immersion thermocouple 830 is installed on the opposite side branch 833 of upper cross 835. The signal from this thermocouple is used by a PARKER AUTOCLAVE ENGINEERS digital controller to regulate the heat output of the furnace and tape heaters wrapped around the test section.

Both the injection tubing 820 and sampling line 810 incorporate a water-jacketed cooling mechanism 815 to keep the lines cool.

FIG. 8B shows a cross sectional view of the test section shown in FIG. 8A, where the cross sectional view of FIG. 8B is taken at the A/A transect shown in FIG. 8A, and where the direction of view of the cross section shown in FIG. 8B is in the direction of the arrows connected to the A/A transect shown in FIG. 8A. This view shows the outer stainless steel tubing 870, which has an outside diameter of 0.5 inches and has a wall thickness of 0.046 inches. Also shown is the stainless steel test specimen rod 840, which has a diameter of 0.25 inches, with noble metal deposited on the surface of the rod 840.

In FIG. 8B, the cross sectional area that lies between the inside face of tubing 870 and the surface of the stainless steel test specimen rod 840, termed the annulus, has an annular area of 0.73 cm².

Test Specimens

The test specimens consisted of 0.25 inch (0.635 cm) diameter 8 inches (20.3 cm) long stainless steel rods covered with Teflon tape to various extents to prevent contact of the stainless steel surface with the test environment. Similar to the preoxidation specimens, a divot was machined one inch (2.54 cm) from the top to set a compression ferrule at this point. Teflon or Rulon glands were machined to seal the specimens. For scoping studies, a platinum foil flag with a surface area of 4.74 cm² was attached to a stainless steel rod. A stainless steel specimen with an exposed metal surface area of 5.38 cm², including the tip surface, was used to obtain baseline data. In addition, one test specimen was prepared by electrochemically depositing 0.1 μg/cm² on the lower one inch (2.54 cm) of a stainless steel specimen abraded with 600 grit emery paper. There were no visible differences between the platinum-treated and the untreated specimens except for the abrasion marks. As before, the remaining surface was covered with Teflon tape to limit the stainless steel surface area exposed to the test environment.

High Temperature Scoping Tests

Several high temperature scoping tests were performed with methanol, hydrogen peroxide and formaldehyde plus hydrogen peroxide to determine what combinations of flow and injectant may produce the most pronounced pH response or concentration changes. Three series of tests were performed using the 3 inch (7.6 cm) long test section as follows.

A) Methanol ($CH_3OH$) Injection

The objectives of these tests was to measure the pH of the test section effluent before and after injection to determine if a measurable change in pH could be detected in the presence of platinum catalyst at two different injectant concentrations.

B) $CH_3OH$ #1 and $CH_3OH$ #2 Test Conditions

Test conditions for $CH_3OH$ Tests #1 and #2 were identical, except the injectant concentrations were 20% $CH_3OH$ for test #1 and 80% $CH_3OH$ for test #2. The test conditions for the methanol injection testing are provided in FIG. 14.

C) Results and Conclusions regarding $CH_3OH$ Scoping Tests 1 and 2

The pH of the test section effluent collected at the sampling point was measured with pH paper having a range of 3 to 6 pH units before and after the 10 minute injection period. The $CH_3OH$ decomposition in the presence of the platinum foil flag specimen at 250° C. was measured by change in the pH. The results were as follows:
  i) Pre-test pH=5
  ii) 20% $CH_3OH$ post-test pH=5
  iii) 80% $CH_3OH$ post-test pH=4.5-5

The observed pH change at two different injectant concentrations was minimal in the presence of platinum. Thus, methanol injection was considered a poor candidate for further consideration.

Formaldehyde (HCHO) Injection
and
Formaldehyde Plus Hydrogen Peroxide ($H_2O_2$) Combined Injection As an alternative to the use of only hydrogen peroxide in the redox reaction, the additional incorporation of formaldehyde (HCHO) in the reaction was considered. The idea of using a combination of formaldehyde and hydrogen peroxide ($H_2O_2$) was tested to determine whether HCHO oxidation to formic acid (HCOOH) by $H_2O_2$ is catalyzed by the presence of platinum on the surface. If it does, then pH decreases to low values more rapidly due to the generation of formic acid. FIGS. 9A, 9B, 10A and 10B illustrate that this is feasible, but the decreased in pH was not very large. The idea was to correlate the extent of the pH decrease with the amount of platinum on the surface. A description of this testing is provided in detail below.

Two tests were conducted, using alternatively either only HCHO injectant solution, or a combination of HCHO and $H_2O_2$ injectant solution, to determine whether these combinations of reagents would yield a more pronounced change in acidity. The methodology used was similar in methodology to the methanol ($CH_3OH$) tests described above.

A) Test Conditions

The test conditions were similar to those of the methanol tests, except that the HCHO Test #1 injectant was 5 ml of 5% formaldehyde+95 ml water; whereas the injectant for HCHO/$H_2O_2$ combination Test #2 was 50 mL water plus 5 mL of 5% formaldehyde plus 10 mL of 7 ppm hydrogen peroxide. As before, the pH was measured with pH paper having a range 3 to 6 pH units. The test conditions for Test #1 and #2 are provided in FIG. 15.

B) HCHO Tests #1 and #2 Results and Conclusions i) Loop pH: Pre-injection pH=5
ii) HCHO Test #1: 10 minute sample pH=4.5
iii) HCHO Test #2: 10 minute sample pH=4

HCHO decomposition in the presence of the platinum foil flag specimen at 250° C. was measured with pH Paper. These pH changes over a 10 minute injection time was minimal with the formaldehyde-only injectant solution.

Addition of 7% hydrogen peroxide slightly enhanced the pH change. A stronger formaldehyde+hydrogen peroxide solution could potentially further enhance the measured pH change. A pH meter was used in subsequent tests to better quantify the observed pH change.

HCHO/$H_2O_2$ Combination Tests #3, #4 and #5 Conditions

Based on the above results, the strength of the HCHO solution was increased to 15%. Three tests under similar conditions, but with different test specimens were run as follows:

Test #3 4.57 cm² platinum foil flag
Test #4 5.38 cm² stainless steel rod
Test #5 5.38 cm² abraded stainless steel rod with 0.1 µg/cm² platinum The injectant was 50 mL water plus 5 mL of 15% formaldehyde plus 10 mL 7 ppm hydrogen peroxide. The injection rate was 50 ccpm. All these test reactions were conducted at high temperature (250° C.) and allowed to react for 10 minutes. All other conditions were the same as those of Tests #1 and #2. The test conditions for these HCHO/$H_2O_2$ combination tests at two flow rates and subsequent low flow tests are summarized in FIG. 16.

An EXTECH® INSTRUMENTS ExStik® EC500 pH meter calibrated with pH 7 and pH 4 buffer solutions was used for pH measurements. Three identical test runs were performed for each condition and the results averaged. The results for the formaldehyde plus hydrogen peroxide (HCHO/$H_2O_2$) combination tests are tabulated below.

| Run | t = 0 min pH | t = 5 min pH | t = 10 min pH |
|---|---|---|---|
| HCHO Test #3 Results, Platinum Foil | | | |
| 3-1 | 6.58 | 4.63 | 4.55 |
| 3-2 | 5.68 | 4.55 | 4.44 |
| 3-3 | 6.21 | 4.68 | 4.44 |
| Average | 6.16 | 4.62 | 4.48 |
| | | | ΔpH = 1.68 |
| HCHO Test #4, Baseline Results (untreated stainless steel) | | | |
| 4-1 | 5.82 | 6.39 | 4.97 |
| 4-2 | 6.58 | 6.69 | 4.22 |
| 4-3 | 6.19 | 5.08 | 4.83 |
| Average | 6.20 | 6.05 | 4.67 |
| | | | ΔpH = 1.52 |
| HCHO Test #3 - Low Flow Results, Platinum Foil | | | |
| 3LF-1 | 6.82 | 5.17 | 4.52 |
| 3LF-2 | 6.7 | 4.82 | 4.61 |
| 3LF-3 | 6.87 | 4.83 | 4.37 |
| Average | 6.80 | 4.94 | 4.50 |
| | | | ΔpH = 2.30 |
| HCHO Test #4 - Low Flow, Baseline Results (untreated stainless steel) | | | |
| 4LF-1 | 6.07 | 4.76 | 4.52 |
| 4LF-2 | 6.06 | 4.74 | 4.43 |
| 4LF-3 | 6.3 | 4.78 | 4.58 |
| Average | 6.14 | 4.76 | 4.51 |
| | | | ΔpH = 1.63 |
| HCHOTest #5, Abraded stainless steel rod with 0.1 µg/cm² platinum | | | |
| 5-1 | 6.29 | 5.42 | 4.43 |
| 5-2 | 6.57 | 4.71 | 4.65 |
| 5-3 | 6.02 | 4.57 | 4.55 |
| Average | 6.29 | 4.90 | 4.54 |
| | | | ΔpH = 1.75 |
| HCHOTest #5 LF, Abraded stainless steel rod with 0.1 µg/cm² platinum | | | |
| 5LF-1 | 6.15 | 4.52 | 4.44 |
| 5LF-2 | 6.12 | 4.87 | 4.51 |
| 5LF-3 | 6.12 | 5.19 | 4.76 |
| Average | 6.13 | 4.86 | 4.57 |
| | | | ΔpH = 1.56 |

These results above expressed as change in pH during the catalysis reactions at the high flow injection rate (50 ccpm) are summarized in the table below.

| High Flow Rate (50 ccpm) change in pH | |
|---|---|
| sample | average change in pH |
| non-catalytic stainless steel rod (Test #4) | 1.52 pH units |
| platinum flag foil test (Test #3) | 1.68 pH units |
| abraded stainless steel rod with 0.1 µg/cm² platinum (Test #5) | 1.75 pH units * highest for the three-test series |

As seen from these values, a measurable increase in acidity was observed after 10 minute HCHO/$H_2O_2$ combined injection with all three specimens. It is evident that the platinum treated stainless steel rod has higher catalytic activity than the platinum foil under these conditions, which is encouraging in terms of the test objectives.

Formaldehyde Plus Hydrogen Peroxide Injection at Low Flow

Comparison of results from Tests #3, #4 and #5 led to a decision to repeat these test at lower chemical injection rates. Thus, the tests were repeated at lower flow rate of 10 ccpm (1 ccpm injectant plus 9 ccpm loop water) to determine if lower flow rates would enhance acidification because of the greater resident time. All other conditions were the same as before (see FIG. 16, and above). The raw data is provided above. These results from above are reexpressed as change in pH during the catalysis reactions at the low flow injection rate (10 ccpm), and are summarized in the table below.

| Low Flow Rate (10 ccpm) change in pH | |
|---|---|
| sample | average change in pH |
| non-catalytic stainless steel rod (Test #4 LF) | 1.63 pH units |
| platinum flag foil test (Test #3 LF) | 2.30 pH units |
| abraded stainless steel rod with 0.1 µg/cm² platinum (Test #5 LF) | 1.56 pH units |

The average change in pH for Test #3 L-F was 2.3 pH units, vs. 1.68 for Test #3 or a slight increase in acidification of 0.62 pH units in the presence of the platinum foil.

The average change in pH for Test #4 L-F was 1.63 pH units vs. 1.52 for Test #4 or a negligible increase in acidification of 0.11 pH units for the stainless steel rod baseline condition.

The average change in pH for Test#5 L-F was 1.56 pH units vs. 1.75 pH units at 50 ccpm for the stainless steel rod with deposited platinum.

These results are the opposite of Test #3 and #4, where acidification was enhanced at higher flow conditions. The lower catalytic activity of the platinum-treated stainless steel rod at lower flow conditions suggests some loss of catalyst that may have occurred during the high flow tests.

Figure 9A:
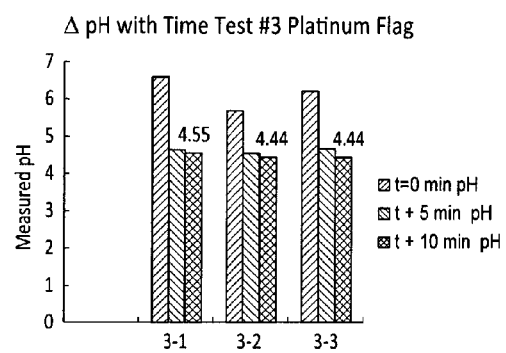
FIGS. 9A and 9B show histograms measuring pH over time for three time points using a platinum flag specimen.
Figure 9B:
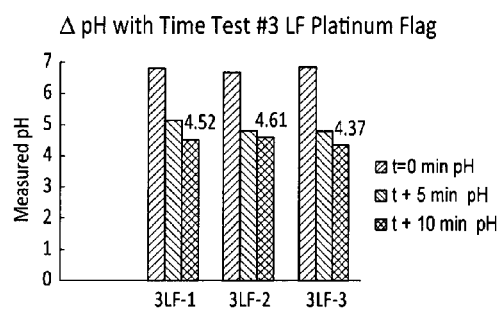

The loss of catalyst can be monitored by evaluating the measured pH at low and high flow rates in that order. FIGS. 9A and 9B show a flat or slightly decreasing pH for the platinum flag specimen in fast flow and low flow systems, respectively, over a 10 minute interval, indicating no loss of catalytic activity. FIG. 9A shows the measured pH After 10 minutes remains constant over time for the platinum flag specimen at 50 ccpm, indicating no loss of catalyst strength (high flow). FIG. 9B shows the measured pH after 10 minutes has a slight downward trend over time for the platinum flag specimen at 10 ccpm, indicating no loss of catalyst strength (low flow).

Figure 10A:
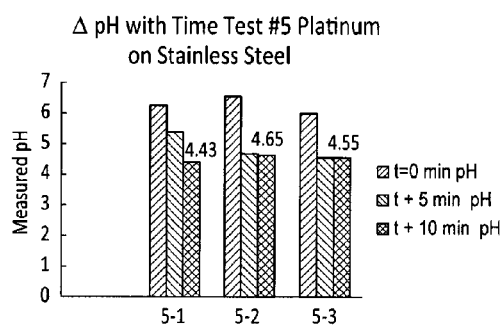
FIGS. 10A and 10B show histograms measuring pH over time for three time points using the abraded plus platinum-treated stainless steel specimen.
Figure 10B:
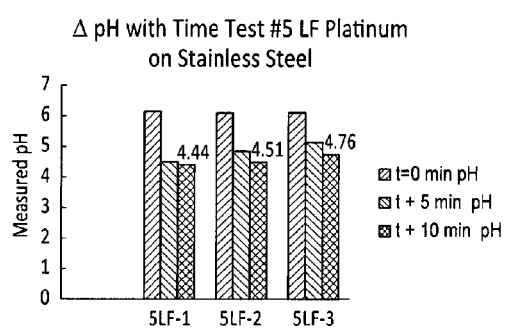

However, FIGS. 10A and 10B show an increasing trend in measured pH, suggesting that catalytic activity is reduced with time. FIG. 10A shows the measured pH over 10 minutes is lowest for the initial run of the abraded plus platinum-treated stainless steel Specimen at 50 ccpm, suggesting potential loss of catalyst over time (high flow). FIG. 10B shows the measured pH continues to trend upwards during subsequent runs of the abraded plus platinum-treated stainless steel specimen at 10 ccpm (low flow), corroborating potential loss of catalyst.

It is noted that during test #5, the platinum-treated specimen was exposed to 50 ccpm flow over 3 hours before the low flow tests were initiated. Therefore, low flow tests need to be conducted before high flow tests to minimize the potential loss of catalyst. Another approach will be to increase the surface roughness to improve the catalyst retention on the surface.

Formaldehyde+Hydrogen Peroxide Tests, Conclusions and Recommendations

The implications of the above results are that:
(a) The formaldehyde decomposition may be a mass transport controlled process in the presence of deposited platinum;
(b) Some of the deposited platinum may have been lost during the higher flow tests and thus, the response at low flow was affected by a lower platinum loading.

The injection tests need to be repeated with a new platinum-treated rod at low flow first and then at high flow to confirm whether platinum loss can account for the observed results. Additional tests with multiple platinum loadings and higher flow rates are needed to further evaluate the capability of this method to differentiate between low levels of platinum loading. Direct measurement of formaldehyde survival fraction by photometric methods should also be evaluated.

If the formaldehyde decomposition is a mass transport process in the presence of deposited platinum, the results are very encouraging for further development of this method for in-situ evaluation of platinum loading.

Hydrogen Peroxide Injection Tests

The objective of the hydrogen peroxide ($H_2O_2$) injection tests was to measure the peroxide survival fraction at elevated temperatures. Preliminary results from the elevated temperature tests showed energetic bubbling at the catalytic surfaces, thus hydrogen peroxide decomposition measurements appear to be an encouraging method to pursue for eventual quantification of catalyst loading.

A) Hydrogen Peroxide Test Conditions

Hydrogen peroxide was injected into the test section at 5 ccpm at two different temperatures, 125° C. and 150° C. Preliminary tests at 175° C. and above indicated that the survival fraction was below the detection limit of the instrument/method used. The hydrogen peroxide catalysis testing conditions are provided in FIG. 17. The testing used 3.5 ppm $H_2O_2$ injection at 5 ccpm at two high temperatures. The injectant and sample concentrations were measured using a CHEMetrics® V-2000 multi-analyte photometer with test kit No. K5513, having a range of 0.15 to 3.00 ppm $H_2O_2$. The actual $H_2O_2$ concentrations used are shown in the last column of FIG. 17. The test specimens were the same ones used for the $CH_3OH$ and HCHO test. However, the hydrogen peroxide decomposition tests were conducted before the formaldehyde tests to prevent possible organics contamination.

B) Hydrogen Peroxide Test Results

Results of hydrogen peroxide injection at 125° C. and 150° C. are provided in a table provided in FIG. 18. The test results taken from FIG. 18 are graphically illustrated in FIG. 11. The bar graph provides the survival fraction for 5 ccpm injection of 3.5 ppm $H_2O_2$ for 10 minutes at 125° C. and 150° C. Results are displayed as the hydrogen peroxide survival fraction for the various test materials, at the two different temperatures tested. These results yield the anticipated trend in hydrogen peroxide decomposition with temperature and platinum loading. This suggests that high priority should be given to further refinement of this technique to quantify in-situ platinum loading tests. Additional tests at higher hydrogen peroxide concentrations and different platinum loadings can help to improve the analytical capability of this method.

While the foregoing disclosure has been described in some detail for purposes of clarity and understanding, it will be clear to one skilled in the art from a reading of this disclosure that various changes in form and materials can be made without departing from the scope of the invention. It is to be understood that the invention is not limited to any of the specifically recited materials or components recited herein, where similar or functionally equivalent materials and components can be substituted and used in the practice of the invention, and remain within the scope of the claimed invention. It is understood that the description and terminology used in the present disclosure is for the purpose of describing particular embodiments of the invention only, and it is not intended that the invention be limited solely to the embodiments described herein.

As used in this specification and the appended claims, singular forms such as "a", "an" and "the" include plural referents unless the content clearly dictates otherwise. For example, reference to "a molecule" includes, as a practical matter, many molecules. All industry and technical terms used herein have the same meaning as commonly understood by one of ordinary skill in the art or industry to which the invention pertains, unless defined otherwise.

All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. A method for detecting a presence of a noble metal associated with a surface of a substrate, the method comprising:
   (a) providing:
      i) a substrate having at least one measurable surface area, said surface area to be assayed for the presence of an associated noble metal; and
      ii) a reaction solution including hydrogen peroxide ($H_2O_2$) at a known concentration; and
   (b) exposing said surface area to the reaction solution, thereby generating a post-reaction solution,
   (c) measuring the concentration of hydrogen peroxide in the post-reaction solution, and
   (d) detecting the presence of said noble metal associated with the surface of the substrate when the measured concentration of hydrogen peroxide in the post-reaction solution is reduced compared to the known hydrogen peroxide concentration in the reaction solution prior to exposing the reaction solution to the surface of the substrate.

2. The method of claim 1, wherein the noble metal is selected from the group consisting of ruthenium, rhodium, palladium, silver, osmium, iridium, platinum, gold, mercury, rhenium and copper.

3. The method of claim 1, wherein the noble metal is platinum.

4. The method of claim 1, wherein the substrate is selected from the group consisting of a rigid substrate and a flexible substrate.

5. The method of claim 1, wherein the substrate is a metal.

6. The method of claim 1, wherein the substrate is a stainless steel.

7. The method of claim 1, wherein the substrate is an inner surface of a substantially cylindrical object.

8. The method of claim 1, wherein the surface of the substrate is an oxidized surface.

9. The method of claim 1, wherein the exposing is at a fixed temperature, or at a fixed pressure, or at both a fixed temperature and fixed pressure.

10. The method of claim 1, wherein the exposing is at a temperature between about 25° C. and 320° C.

11. The method of claim 1, further comprising step (e) correlating the measured concentration of hydrogen peroxide in the post-reaction solution with a noble metal loading value on the surface of the substrate.

12. The method of claim 11, where correlating comprises
    (i) generating a predetermined correspondence between the concentration of hydrogen peroxide in a post-reaction solution with calibrated noble metal loading values, and
    (ii) deriving the noble metal loading value associated with the surface of the substrate from the measured concentration of hydrogen peroxide in the post-reaction solution using the predetermined correspondence.

13. A method for detecting the presence of a noble metal associated with a surface of a channel, the method comprising:
    (a) providing:
       i) a reaction solution including hydrogen peroxide ($H_2O_2$) at a known concentration; and
       ii) a channel housing a liquid flow, the channel comprising an injection port at a first terminus and a sampling port at a second terminus,
    (b) delivering the reaction solution into the liquid flow through the injection port, thereby exposing the surface of the channel to the reaction solution and generating a post-reaction liquid flow,
    (c) sampling the post-reaction liquid flow through the sampling port,
    (d) measuring the concentration of hydrogen peroxide in the post-reaction liquid flow, and
    (e) detecting the presence of said noble metal associated with the surface of the channel when hydrogen peroxide decomposition is detected, where decomposition is detected by comparing the hydrogen peroxide concentration in the post-reaction liquid flow to the hydrogen peroxide concentration in the reaction solution at the time of delivering the reaction solution to the liquid flow.

14. The method of claim 13, wherein the channel is a substantially cylindrical structure.

15. The method of claim 13, wherein the channel is a stainless steel channel.

16. The method of claim 13, wherein the noble metal is platinum.

17. The method of claim 13, further comprising step (f) correlating the measured concentration of hydrogen peroxide in the post-reaction liquid flow with a noble metal loading value on the surface of the channel.

18. A system for detecting the presence of a noble metal associated with a surface of a channel, the system comprising:
    (a) a channel housing a liquid flow;
    (b) a reaction solution including hydrogen peroxide ($H_2O_2$) at a known concentration,
    (c) an injection port operably coupled to the channel, where the reaction solution is deliverable to the liquid flow through the injection port,
    (d) a sampling port operably coupled to the channel at a position that is downstream of the injection port relative to the direction of liquid flow, where a sample from the liquid flow is extractable through the sampling port after reaction solution is delivered to the liquid flow through the injection port,
    (e) instrumentation configured for measuring the concentration of hydrogen peroxide in the sample of the liquid flow extracted through the sampling port, and
    (f) a correlation module configured for correlating a hydrogen peroxide concentration in the sample of the liquid flow measured by the instrumentation with detection of the presence of the noble metal, where correlating comprises detecting hydrogen peroxide decomposition by comparing the hydrogen peroxide concentration in the post-reaction liquid flow to the hydrogen peroxide concentration in the reaction solution.

* * * * *